US009316581B2

(12) United States Patent
Mander et al.

(10) Patent No.: US 9,316,581 B2
(45) Date of Patent: Apr. 19, 2016

(54) METHOD, APPARATUS, AND ARTICLE TO FACILITATE EVALUATION OF SUBSTANCES USING ELECTROMAGNETIC ENERGY

(71) Applicant: Visualant, Inc., Seattle, WA (US)

(72) Inventors: Richard Ian Mander, Bainbridge Island, WA (US); Thomas A. Furness, III, Seattle, WA (US); Brian T. Schowengerdt, Seattle, WA (US); Michael Vivian Denton, Christchurch (NZ); Allan David Beach, Prebbleton (NZ); Alan Charles Tompkins, Ferny Grove (AU)

(73) Assignee: Visualant, Inc., Seattle, WA (US)

( * ) Notice: Subject to any disclaimer, the term of this patent is extended or adjusted under 35 U.S.C. 154(b) by 0 days.

(21) Appl. No.: 13/796,835

(22) Filed: Mar. 12, 2013

(65) Prior Publication Data

US 2014/0218718 A1    Aug. 7, 2014

Related U.S. Application Data

(60) Provisional application No. 61/760,527, filed on Feb. 4, 2013.

(51) Int. Cl.
*G01J 5/00* (2006.01)
*G01N 21/27* (2006.01)
*G01N 21/31* (2006.01)

(52) U.S. Cl.
CPC .............. *G01N 21/274* (2013.01); *G01N 21/31* (2013.01)

(58) Field of Classification Search
USPC ...................................................... 250/338.1
See application file for complete search history.

(56) References Cited

U.S. PATENT DOCUMENTS

| 3,499,158 A | 3/1970 | Lavine et al. |
| 3,504,164 A | 3/1970 | Farrell et al. |
| 3,582,659 A | 6/1971 | Dekker |
| 3,679,449 A | 7/1972 | Nagot et al. |
| 3,822,098 A | 7/1974 | Rudder et al. |

(Continued)

FOREIGN PATENT DOCUMENTS

| EP | 2 266 630 A1 | 12/2010 |
| GB | 1 470 737 | 4/1977 |

(Continued)

OTHER PUBLICATIONS

"Color Technology Beyond the Visible Spectrum Creating Solutions for Product Authentication: Extraordinary Investment Opportunity & 12 month Roadmap," Visualant Inc., Seattle, Washington, Nov. 17, 2006, 10 pages.

(Continued)

*Primary Examiner* — David Porta
*Assistant Examiner* — Edwin Gunberg
(74) *Attorney, Agent, or Firm* — Seed IP Law Group PLLC

(57) ABSTRACT

Sampling device geometry reduces specular reflectance, using lenses to focus electromagnetic energy to predominately return scattered rather than reflected electromagnetic energy to detector(s), reducing effect of non-matte surfaces and/or window. Sampling device includes inherent automatic optical calibration, and optionally thermal calibration. Calibration detectors are optically isolated with respective emitters.

54 Claims, 13 Drawing Sheets

(56) References Cited

U.S. PATENT DOCUMENTS

| | | | |
|---|---|---|---|
| 3,867,039 A | 2/1975 | Nelson | |
| 3,922,090 A | 11/1975 | Fain | |
| 3,942,185 A | 3/1976 | Lebailly | |
| 3,994,590 A | 11/1976 | Di Martini et al. | |
| 4,082,188 A | 4/1978 | Grimmell et al. | |
| 4,098,940 A | 7/1978 | Groh et al. | |
| 4,120,445 A | 10/1978 | Carrier et al. | |
| 4,183,989 A | 1/1980 | Tooth | |
| 4,241,738 A | 12/1980 | Lübbers et al. | |
| 4,277,514 A | 7/1981 | Sugiura et al. | |
| 4,325,981 A | 4/1982 | Sugiura et al. | |
| 4,531,117 A | 7/1985 | Nourse et al. | |
| 4,652,913 A | 3/1987 | Saitoh et al. | |
| 4,678,338 A | 7/1987 | Kitta et al. | |
| 4,760,250 A | 7/1988 | Loeppert | |
| 4,830,501 A | 5/1989 | Terashita | |
| 4,921,278 A | 5/1990 | Shiang et al. | |
| 4,952,061 A | 8/1990 | Edgar | |
| 5,137,364 A | 8/1992 | McCarthy | |
| 5,304,813 A | 4/1994 | De Man | |
| 5,325,167 A | 6/1994 | Melen | |
| 5,353,052 A | 10/1994 | Suzuki et al. | |
| 5,377,000 A | 12/1994 | Berends | |
| 5,576,627 A | 11/1996 | McEwan | |
| 5,619,326 A | 4/1997 | Takamatsu et al. | |
| 5,637,275 A | 6/1997 | Carey et al. | |
| 5,844,680 A | 12/1998 | Sperling | |
| 5,924,981 A * | 7/1999 | Rothfritz et al. | 600/306 |
| 5,926,282 A | 7/1999 | Knobloch et al. | |
| 5,933,244 A | 8/1999 | Kiritchenko | |
| 5,946,006 A | 8/1999 | Tajika et al. | |
| 5,966,217 A | 10/1999 | Roe et al. | |
| 5,969,814 A | 10/1999 | Barber et al. | |
| 6,020,583 A | 2/2000 | Walowit et al. | |
| 6,035,246 A | 3/2000 | Wagner | |
| 6,038,024 A | 3/2000 | Berner | |
| 6,054,021 A | 4/2000 | Kurrle et al. | |
| 6,121,627 A | 9/2000 | Tulip | |
| 6,142,629 A | 11/2000 | Adel et al. | |
| 6,165,609 A | 12/2000 | Curatolo | |
| 6,172,745 B1 | 1/2001 | Voser et al. | |
| 6,176,522 B1 | 1/2001 | Jackson | |
| 6,255,948 B1 | 7/2001 | Wolpert et al. | |
| 6,384,918 B1 | 5/2002 | Hubble, III et al. | |
| 6,421,553 B1 | 7/2002 | Costa et al. | |
| 6,437,326 B1 | 8/2002 | Yamate et al. | |
| 6,439,688 B1 | 8/2002 | Vives et al. | |
| 6,449,045 B1 | 9/2002 | Mestha | |
| 6,494,557 B1 | 12/2002 | Kato et al. | |
| 6,556,932 B1 | 4/2003 | Mestha et al. | |
| 6,560,352 B2 | 5/2003 | Rowe et al. | |
| 6,560,546 B1 | 5/2003 | Shenk et al. | |
| 6,584,435 B2 | 6/2003 | Mestha et al. | |
| 6,621,576 B2 | 9/2003 | Tandon et al. | |
| 6,633,382 B2 | 10/2003 | Hubble, III et al. | |
| 6,639,699 B2 | 10/2003 | Matsuyama | |
| 6,690,465 B2 | 2/2004 | Shimizu et al. | |
| 6,718,046 B2 | 4/2004 | Reed et al. | |
| 6,721,440 B2 | 4/2004 | Reed et al. | |
| 6,721,629 B2 | 4/2004 | Wendling et al. | |
| 6,724,912 B1 | 4/2004 | Carr et al. | |
| 6,731,785 B1 | 5/2004 | Mennie et al. | |
| 6,744,909 B1 | 6/2004 | Kostrzewski et al. | |
| 6,748,533 B1 | 6/2004 | Wu et al. | |
| 6,757,406 B2 | 6/2004 | Rhoads | |
| 6,763,124 B2 | 7/2004 | Alattar et al. | |
| 6,765,663 B2 | 7/2004 | Byren et al. | |
| 6,782,115 B2 | 8/2004 | Decker et al. | |
| 6,788,800 B1 | 9/2004 | Carr et al. | |
| 6,798,517 B2 | 9/2004 | Wagner et al. | |
| 6,804,376 B2 | 10/2004 | Rhoads et al. | |
| 6,804,377 B2 | 10/2004 | Reed et al. | |
| 6,809,855 B2 | 10/2004 | Hubble, III et al. | |
| 6,819,775 B2 | 11/2004 | Amidror et al. | |
| 6,832,003 B2 | 12/2004 | McGrew | |
| 6,835,574 B2 | 12/2004 | Neilson et al. | |
| 6,870,620 B2 | 3/2005 | Faupel et al. | |
| 6,882,737 B2 | 4/2005 | Lofgren et al. | |
| 6,888,633 B2 | 5/2005 | Vander Jagt et al. | |
| 6,930,773 B2 | 8/2005 | Cronin et al. | |
| 6,937,323 B2 | 8/2005 | Worthington et al. | |
| 6,968,337 B2 | 11/2005 | Wold | |
| 6,980,704 B2 | 12/2005 | Kia et al. | |
| 6,992,775 B2 | 1/2006 | Soliz et al. | |
| 6,993,535 B2 | 1/2006 | Bolle et al. | |
| 6,995,839 B1 | 2/2006 | Shapiro | |
| 6,996,478 B2 | 2/2006 | Sunshine et al. | |
| 7,001,038 B2 | 2/2006 | Bock et al. | |
| 7,003,132 B2 | 2/2006 | Rhoads | |
| 7,003,141 B1 | 2/2006 | Lichtermann et al. | |
| 7,005,661 B2 | 2/2006 | Yamaguchi et al. | |
| 7,006,204 B2 | 2/2006 | Coombs et al. | |
| 7,008,795 B2 | 3/2006 | Yerazunis et al. | |
| 7,012,695 B2 | 3/2006 | Maier et al. | |
| 7,016,717 B2 | 3/2006 | Demos et al. | |
| 7,018,204 B2 | 3/2006 | Jung et al. | |
| 7,023,545 B2 | 4/2006 | Slater | |
| 7,026,600 B2 | 4/2006 | Jamieson et al. | |
| 7,027,134 B1 | 4/2006 | Garcia-Rubio et al. | |
| 7,027,165 B2 | 4/2006 | De Haas et al. | |
| 7,027,619 B2 | 4/2006 | Pavlidis et al. | |
| 7,031,555 B2 | 4/2006 | Troyanker | |
| 7,032,988 B2 | 4/2006 | Darby et al. | |
| 7,035,873 B2 | 4/2006 | Weare | |
| 7,038,766 B2 | 5/2006 | Kerns et al. | |
| 7,041,362 B2 | 5/2006 | Barbera-Guillem | |
| 7,044,386 B2 | 5/2006 | Berson | |
| 7,046,346 B2 | 5/2006 | Premjeyanth et al. | |
| 7,046,842 B2 | 5/2006 | Lin et al. | |
| 7,049,597 B2 | 5/2006 | Bodkin | |
| 7,052,730 B2 | 5/2006 | Patel et al. | |
| 7,052,920 B2 | 5/2006 | Ushio et al. | |
| 7,058,200 B2 | 6/2006 | Donescu et al. | |
| 7,058,530 B1 | 6/2006 | Miller et al. | |
| 7,061,652 B2 | 6/2006 | Kurita et al. | |
| 7,063,260 B2 | 6/2006 | Mossberg et al. | |
| 7,130,444 B2 | 10/2006 | Honsinger et al. | |
| 7,154,603 B2 * | 12/2006 | Banks | 356/417 |
| 7,155,068 B2 | 12/2006 | Zhang et al. | |
| 7,170,606 B2 | 1/2007 | Yerazunis | |
| 7,171,680 B2 | 1/2007 | Lange | |
| 7,252,241 B2 | 8/2007 | Yamada | |
| 7,259,853 B2 | 8/2007 | Hubble, III et al. | |
| 7,285,158 B2 | 10/2007 | Iwanami et al. | |
| 7,307,752 B1 | 12/2007 | Mestha et al. | |
| 7,313,427 B2 | 12/2007 | Benni | |
| 7,317,814 B2 | 1/2008 | Kostrzewski et al. | |
| 7,319,775 B2 | 1/2008 | Sharma et al. | |
| 7,359,804 B2 | 4/2008 | Williams et al. | |
| 7,383,261 B2 | 6/2008 | Mestha et al. | |
| 7,406,184 B2 | 7/2008 | Wolff et al. | |
| 7,440,620 B1 | 10/2008 | Aartsen | |
| 7,474,407 B2 | 1/2009 | Gutin | |
| 7,483,548 B2 | 1/2009 | Nakano et al. | |
| 7,570,988 B2 | 8/2009 | Ramanujam et al. | |
| 7,733,490 B2 | 6/2010 | Goodwin et al. | |
| 7,830,510 B2 | 11/2010 | Liu et al. | |
| 7,996,173 B2 | 8/2011 | Schowengerdt et al. | |
| 8,064,286 B2 | 11/2011 | Rønnekleiv et al. | |
| 8,076,630 B2 * | 12/2011 | Schowengerdt et al. | 250/221 |
| 8,081,304 B2 | 12/2011 | Furness, III et al. | |
| 8,285,510 B2 | 10/2012 | Schowengerdt et al. | |
| 8,368,878 B2 | 2/2013 | Furness, III et al. | |
| 8,542,418 B2 | 9/2013 | Chandu et al. | |
| 8,583,394 B2 | 11/2013 | Schowengerdt et al. | |
| 8,796,627 B2 | 8/2014 | Rockwell et al. | |
| 2002/0146146 A1 | 10/2002 | Miolla et al. | |
| 2003/0031347 A1 | 2/2003 | Wang | |
| 2003/0045798 A1 | 3/2003 | Hular et al. | |
| 2003/0063772 A1 | 4/2003 | Smith et al. | |
| 2003/0151611 A1 | 8/2003 | Turpin et al. | |
| 2003/0156752 A1 | 8/2003 | Turpin et al. | |
| 2003/0158617 A1 | 8/2003 | Turpin et al. | |
| 2003/0158788 A1 | 8/2003 | Turpin et al. | |

(56) References Cited

U.S. PATENT DOCUMENTS

| | | |
|---|---|---|
| 2003/0174882 A1 | 9/2003 | Turpin et al. |
| 2003/0235919 A1 | 12/2003 | Chandler |
| 2004/0071311 A1 | 4/2004 | Choi et al. |
| 2004/0101158 A1 | 5/2004 | Butler |
| 2004/0101159 A1 | 5/2004 | Butler |
| 2004/0142484 A1 | 7/2004 | Berlin et al. |
| 2005/0094127 A1 | 5/2005 | O'mahony et al. |
| 2006/0059013 A1 | 3/2006 | Lowe |
| 2006/0077392 A1 | 4/2006 | Hebert et al. |
| 2006/0109475 A1* | 5/2006 | Misener et al. ............ 356/446 |
| 2006/0161788 A1 | 7/2006 | Turpin et al. |
| 2007/0078610 A1 | 4/2007 | Adams et al. |
| 2007/0222973 A1 | 9/2007 | Hoshiko et al. |
| 2008/0025028 A1* | 1/2008 | Gloisten et al. ............ 362/294 |
| 2008/0171925 A1 | 7/2008 | Xu et al. |
| 2008/0212087 A1 | 9/2008 | Mannhardt et al. |
| 2008/0252066 A1 | 10/2008 | Rapoport et al. |
| 2010/0282982 A1* | 11/2010 | Schreiber et al. .......... 250/459.1 |
| 2011/0223655 A1 | 9/2011 | Lapota et al. |
| 2012/0037817 A1 | 2/2012 | Vondras et al. |
| 2012/0072176 A1 | 3/2012 | Schowengerdt et al. |
| 2012/0288951 A1 | 11/2012 | Acharya et al. |
| 2013/0208260 A1 | 8/2013 | Furness, III et al. |
| 2013/0215168 A1 | 8/2013 | Furness, III et al. |
| 2014/0063239 A1 | 3/2014 | Furness, III et al. |
| 2014/0203184 A1 | 7/2014 | Purdy et al. |
| 2014/0233015 A1 | 8/2014 | Mander et al. |
| 2014/0333920 A1 | 11/2014 | Mander et al. |

FOREIGN PATENT DOCUMENTS

| | | |
|---|---|---|
| JP | 10-508940 A | 9/1998 |
| JP | 2005-214835 A | 8/2005 |
| WO | 91/05459 A1 | 5/1991 |
| WO | 96/07886 A1 | 3/1996 |
| WO | 00/12229 A1 | 3/2000 |
| WO | 03/069884 A2 | 8/2003 |
| WO | 2004/089640 A2 | 10/2004 |
| WO | 2006/050367 A2 | 5/2006 |
| WO | 2008/016590 A2 | 2/2008 |
| WO | 2013/043737 A1 | 3/2013 |
| WO | 2013/119822 A1 | 8/2013 |
| WO | 2013/119824 A1 | 8/2013 |
| WO | 2014/121267 A2 | 8/2014 |
| WO | 2014/130857 A1 | 8/2014 |

OTHER PUBLICATIONS

Cri Nuance Multispectral Imaging System, URL=http://www.cri-inc.com/products/nuance.asp, download date Jan. 30, 2007, 2 pages.

Cri Products Components, URL=http://www.cri-inc.com/products/components.asp, download date Jan. 30, 2007, 5 pages.

Furness III, "Systems, Methods and Articles Related to Machine-Readable Indicia and Symbols," U.S. Appl. No. 61/597,593, filed Feb. 10, 2012, 89 pages.

Furness III, "Area Surveillance Systems and Methods," U.S. Appl. No. 61/597,586, filed Feb. 10, 2012, 72 pages.

Furness, III et al., "Method, Apparatus, and Article to Facilitate Evaluation of Objects Using Electromagnetic Energy," U.S. Appl. No. 60/871,639, filed Dec. 22, 2006, 140 pages.

Furness, III et al., "Method, Apparatus, and Article to Facilitate Evaluation of Objects Using Electromagnetic Energy," U.S. Appl. No. 60/883,312, filed Jan. 3, 2007, 147 pages.

Furness, III et al., "Method, Apparatus, and Article to Facilitate Evaluation of Objects Using Electromagnetic Energy," U.S. Appl. No. 60/890,446, filed Feb. 16, 2007, 155 pages.

Furness, III et al., "Methods, Apparatus, and Article to Facilitate Evaluation of Objects Using Electromagnetic Energy," U.S. Appl. No. 60/834,589, filed Jul. 31, 2006, 135 pages.

International Search Report, mailed Jun. 21, 2007, for PCT/US2005/039495, 1 page.

International Search Report, mailed Jul. 23, 2008, for PCT/US2007/017082, 1 page.

International Search Report, mailed Feb. 25, 2013, for PCT/US2012/056135, 3 pages.

International Search Report, mailed May 15, 2013, for PCT/US2013/025162, 3 pages.

International Search Report, mailed May 13, 2013, for PCT/US2013/025164, 3 pages.

International Search Report and Written Opinion, mailed Jun. 29, 2014, for PCT/US2014/017776, 11 pages.

International Search Report, mailed Dec. 8, 2014, for PCT/US14/14656, 2 pages.

International Search Report, mailed Sep. 4, 2014, for PCT/US2014/024100, 3 pages.

Japanese Office Action with English Translation for Corresponding Japanese Patent Application No. 2009-522834, mailed Aug. 7, 2012, 8 pages.

Mander et al., "A Device for Evaluation of Fluids Using Electromagnetic Energy," U.S. Appl. No. 61/767,716, filed Feb. 21, 2013, 61 pages.

Mander et al., "Method, Apparatus, and Article to Facilitate Evaluation of Substances Using Electromagnetic Energy," U.S. Appl. No. 61/760,527, filed Feb. 4, 2013, 72 pages.

Mander et al., "Systems and Methods for Fluid Analysis Using Electromagnetic Energy," U.S. Appl. No. 61/777,750, filed Mar. 12, 2013, 39 pages.

Purdy, "Fluid Medium Sensor System and Method," U.S. Appl. No. 61/538,617, filed Sep. 23, 2011, 75 pages.

Schowengerdt et al., "Method, Apparatus, and Article to Facilitate Distributed Evaluation of Objects Using Electromagnetic Energy," U.S. Appl. No. 60/834,662, filed Jul. 31, 2006, 96 pages.

Schowengerdt et al., "System and Method of Evaluating an Object Using Electromagnetic Energy," U.S. Appl. No. 60/820,938, filed Jul. 31, 2006, 69 pages.

Schowengerdt, "Brief Technical Description of the Cyclops Spectral Analysis and Authentication System," Visualant Inc. memorandum, not disclosed prior to Dec. 22, 2006, 2 pages.

Thomas, "A Beginner's Guide to ICP-MS—Part V: The Ion Focusing System," *Spectroscopy 16* (9):38-44, Sep. 2001.

Turpin et al., "Full Color Spectrum Object Authentication Methods and Systems," U.S. Appl. No. 60/732,163, filed Oct. 31, 2005, 198 pages.

Turpin, "Full Color Spectrum Object Authentication Methods and Systems," U.S. Appl. No. 60/623,881, filed Nov. 1, 2004, 114 pages.

Vrhel, "An LED based spectrophotometric instrument," *Color Imaging: Device-Independent Color, Color Hardcopy, and Graphic Arts IV, Proceedings of the SPIE 3648*:226-236, Jan. 1999.

Written Opinion, mailed Jun. 21, 2007, for PCT/US2005/039495, 5 pages.

Written Opinion, mailed Jul. 23, 2008, for PCT/US2007/017082, 3 pages.

Written Opinion, mailed Feb. 25, 2013, for PCT/US2012/056135, 4 pages.

Written Opinion, mailed May 15, 2013, for PCT/US2013/025162, 7 pages.

Written Opinion, mailed May 13, 2013, for PCT/US2013/025164, 6 pages.

Written Opinion, mailed Dec. 8, 2014, for PCT/US14/14656, 10 pages.

Written Opinion, mailed Sep. 4, 2014, for PCT/US2014/024100, 4 pages.

* cited by examiner

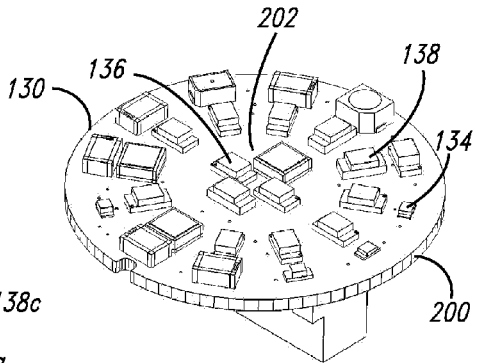
FIG. 2A
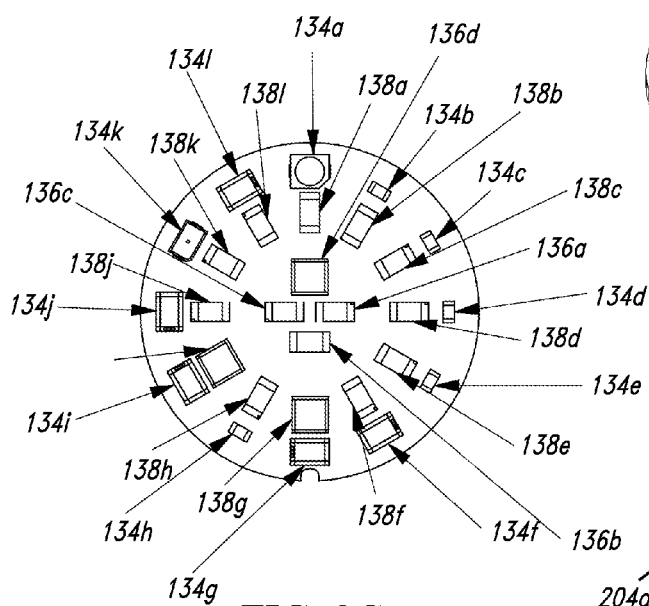
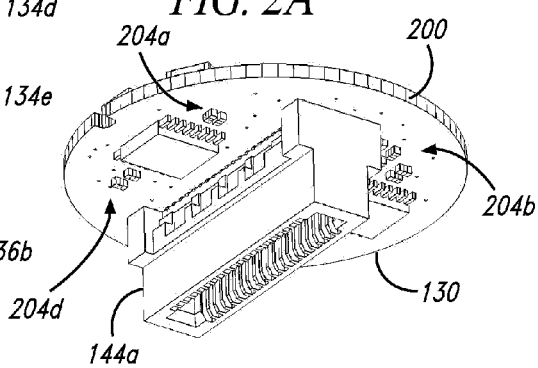
FIG. 2B
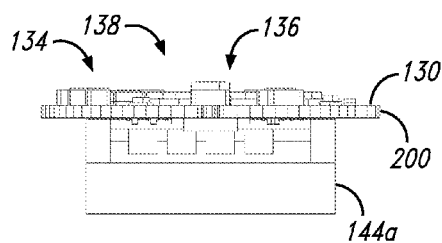
FIG. 2E
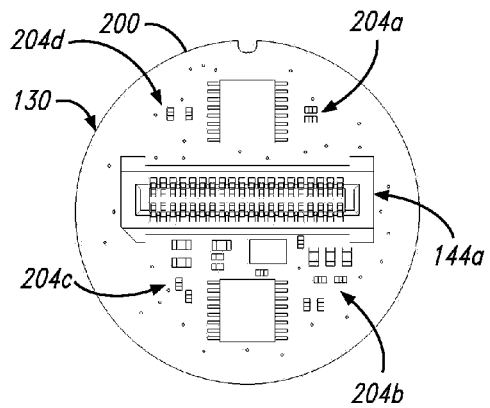
FIG. 2D
FIG. 2C
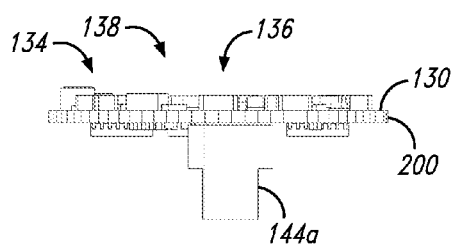
FIG. 2F

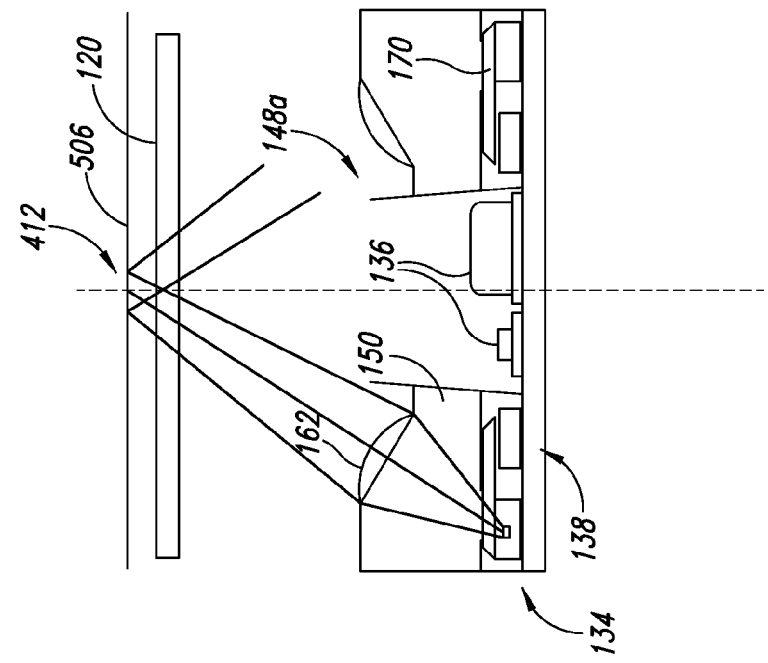
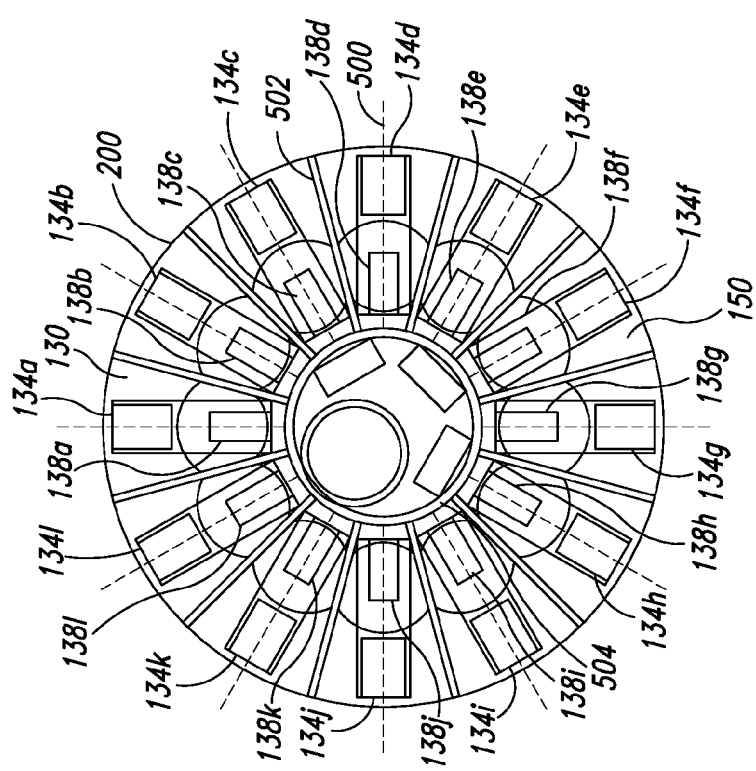
FIG. 5B
FIG. 5A

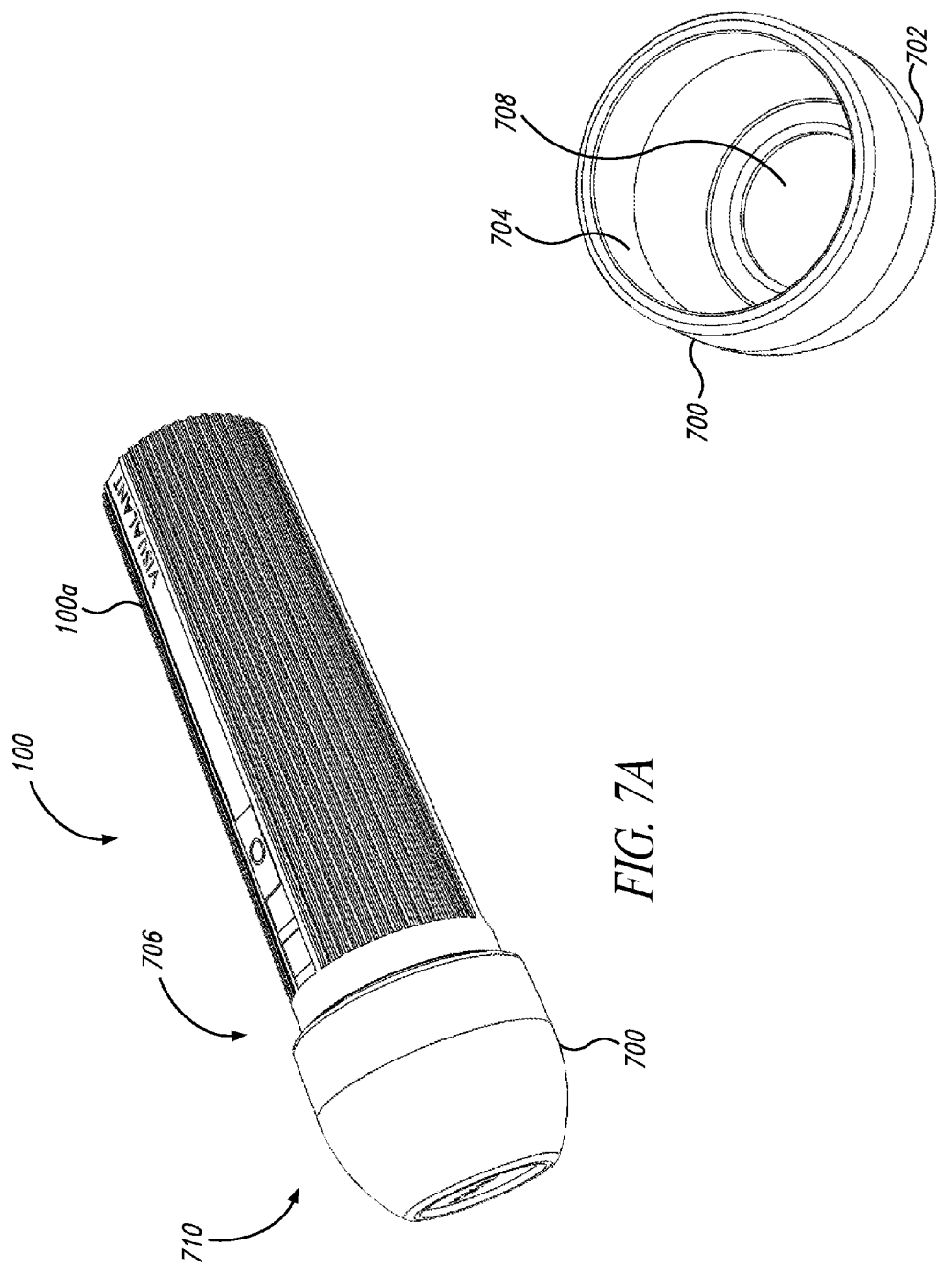

METHOD, APPARATUS, AND ARTICLE TO FACILITATE EVALUATION OF SUBSTANCES USING ELECTROMAGNETIC ENERGY

BACKGROUND

1. Field

This disclosure generally relates to evaluation systems, and more particularly to systems that evaluate characteristics of substances using electromagnetic energy.

2. Description of the Related Art

Various systems employ spectral analysis returned from a sample of a substance to analyze the sample and/or recognize the substance.

For example, U.S. Pat. No. 8,076,630 describes systems and methods of evaluating objects using electromagnetic energy. In particular, U.S. Pat. No. 8,076,630 teaches a system for evaluating subject objects, the system which includes at least one physical source operable to emit electromagnetic energy and driver electronics drivingly coupled to at least one physical source. The driver electronics drive at least one physical source as a number of logical sources, using an electromagnetic forcing function where the number of logical sources is greater than the number of physical sources. In addition, the system includes a sensor to receive an electromagnetic response from at least a portion of an evaluation object illuminated by one or more physical sources operated as logical sources, and convert the electromagnetic response to a test response signal indicative of the electromagnetic response of the evaluation object.

Also for example, U.S. Pat. No. 7,996,173 describes methods, apparatus and articles to facilitate distributed evaluation of objects using electromagnetic energy. In particular, U.S. Pat. No. 7,996,173 teaches that objects such as manufactured goods or articles, works of art, media such as identification documents, legal documents, financial instruments, transaction cards, other documents, and/or biological tissue are sampled via sequential illumination in various bands of the electromagnetic spectrum, and a test response to the illumination is analyzed with respect to reference responses of reference objects. U.S. Pat. No. 7,996,173 teaches that the sequence may be varied. For instance, the sequence may define an activation order, a drive level and/or temperature for operating one or more sources. Illumination may be in visible, infrared, ultraviolet, or other portions of the electromagnetic spectrum. U.S. Pat. No. 7,996,173 further teaches that elements of the evaluation system may be remote from one another, for example communicatively coupled via a network.

As a further example, U.S. Pat. No. 8,081,304 describes the use of spectral information in process control and/or quality control of goods and articles. In particular, U.S. Pat. No. 8,081,304 describes the use of spectral information in process control and/or quality control of media, for example, financial instruments, identity documents, legal documents, medical documents, financial transaction cards, and/or other media, fluids, for example lubricants, fuels, coolants, or other materials that flow, and in machinery, for example, vehicles, motors, generators, compressors, presses, drills and/or supply systems. U.S. Pat. No. 8,081,304 further describes the use of spectral information in identifying biological tissue and/or facilitate diagnosis based on biological tissue.

The above described patents are only representative.

BRIEF SUMMARY

It may be useful to analyze substances to determine various physical characteristics of the substances and/or to recognize the substance as being or not being a specific type of substance. In order to reliably analyze and/or recognize a substance, it may be useful to sample the substance at a relatively large number of distinct wavelengths or bands of wavelengths of electromagnetic energy. The wavelengths may, for example, include some or all wavelengths in an optical portion of the electromagnetic spectrum, from near-infrared (N-IR) to near-ultraviolet (N-UV), inclusive, including a visible portion that is visually perceptible to humans. Accurately performing such analysis or recognition typically requires a relatively large number of distinct sources or emitters, e.g., solid-state sources of electromagnetic energy such as light emitting diodes (LEDs), each operable to emit electromagnetic energy in a respective range or band of wavelengths which may or may not partially overlap with one another.

To achieve a high degree of reliability it may be advantageous to perform calibration. Calibration can address issues raised by variations in source performance, for example, variations in wavelength output due to age, changes in temperature, or even in manufacturing tolerances (e.g., from batch to batch from a given emitter manufacturer). However, to be effective, calibration will typically need to be performed automatically, preferably with little to no user or operator interaction. Also, to be effective, calibration with respect to sources or emitters should employ calibration targets or samples with known characteristics (e.g., spectral characteristics) which are stable and do not vary over time.

Providing for automatic calibration may enhance the accuracy of sampling devices. Providing for automatic calibration in a compact form factor may further allow for small, portable sampling devices, which are highly accurate.

Scattering is a physical process in which some forms of electromagnetic radiation deviate from a straight path or trajectory due to localized non-uniformities in a medium through which the electromagnetic radiation passes. As commonly used, this also includes deviation of reflected electromagnetic radiation from an angle predicted by the law of reflection. Reflections that undergo scattering are often called diffuse reflections, while unscattered reflections are called specular (e.g., mirror-like) reflections.

There are two principal scattering mechanisms, Rayleigh scattering and Raman scattering. In Rayleigh scattering most photons are elastically scattered such that scattered photons have the same kinetic energy (frequency and wavelength) as the incident photons. In Raman scattering scattered photons are scattered by excitation, having a frequency that is different from, and usually lower than, that of the incident photons. For any given sample both mechanisms will typically apply, with Raman scattering making up a smaller fraction of the total scattering. Raman is particularly useful in analyzing composition of liquids, gases and solids.

Lambertian reflectance characterizes an ideal diffusely reflecting surface. An apparent brightness of such an ideal diffusely reflecting surface is the same regardless of angle of view. Technically, the luminance of a surface is isotropic, and luminous intensity obeys Lambert's cosine law. Lambertian reflection from polished (i.e., glossy or non-matte) surfaces is typically accompanied by specular reflection. The luminance of a polished or glossy surface is largest when viewed at a perfect reflection direction (i.e., where a direction of the reflected light is a reflection of the direction of the incident light in the surface). The luminance falls off sharply as direction (i.e., angle) changes.

To achieve a high degree of accuracy, in some implementations it may be advantageous to eliminate specular reflection or at least allow discrimination between scattered and specular reflection. Such reflection may be from a sample or specimen itself, a surface on which the sample or specimen resides, or even a component of a sampling device, for instance, a protective window or lens cover.

To achieve a high degree of accuracy, in some implementations it may be advantageous to separate specular reflection from diffuse reflection, detecting each separately.

Sampling devices employing automatic calibration and/or separation of specular reflection may be effective employed in the object analysis, evaluation or identification to various applications, for example: manufacturing process control, quality assurance, media authentication, biological tissue recognition, identification, verification, authentication, classification, and/or diagnostics.

A sampling system may be summarized as including a sampling device, the sampling device including: a housing; a plurality of emitters received in the housing, each of the emitters selectively operable to emit electromagnetic energy in a respective range of wavelengths in an optical portion of the electromagnetic spectrum, the ranges of wavelengths of at least some of the emitters different from the ranges of wavelengths of others of the emitters; at least one primary sampling sensor received in the housing and positioned to receive electromagnetic energy returned to the sampling device by a sample, if any, illuminated by the electromagnetic energy emitted by at least one of the emitters, the at least one primary sampling sensor responsive to a number of wavelengths of electromagnetic energy returned to the sampling device; and at least one calibration sensor received in the housing and positioned to receive electromagnetic energy emitted by at least one of the emitters substantially free of electromagnetic energy returned to the sampling device, the at least one calibration sensor responsive to a number of wavelengths of electromagnetic energy emitted by the emitters.

The at least one calibration sensor may include at least one calibration sensor per emitter. The calibration sensors may be matched to the output of the respective emitters.

The sampling system may further include an endless array of compartments which isolate each of a number of the emitters from one another.

The endless array of compartments may be formed as a unitary single-piece annular array arranged about a central passage. Each of the calibration sensors may be positioned in a respective one of the compartments of the endless array of compartments. Each compartment may include a slot that limits entrance into the respective compartment of spectral illumination returned to the sampling device from the specimen, if any. The respective calibration sensors may be positioned in the respective compartments shielded from the respective slots. The compartments may each have walls, the entirety of the wall(s) colored black.

The sampling system may further include at least one optical tap that provides a respective distinct optical path between a position at least proximate respective ones of the emitters and respective ones of the calibration sensors.

The at least one optical tap may be an integral portion of the endless array of compartments. The at least one optical tap may consist of a high grade optical resin (e.g., cyclic polyolefin).

The compartments may each have walls, a portion of the wall(s) colored black and a portion of the wall(s) colored a reference color. The calibration sensors may be matched to the output of the respective emitter with which the calibration sensor is compartmentalized. The calibration sensors may each consist of a single optical sensor chip that detects from near-infrared (N-IR) through near-ultraviolet (N-UV) wavelengths of electromagnetic energy.

The sampling system may further include a first circuit board on which the emitters are arrayed in a circular array; and an annular array of distinct lenses physically coupled to one another as an integral one-piece construction which includes a circular band that physically couples the distinct lenses to one another, each of the distinct lenses closely received in a respective one of the compartments of the endless array of compartments.

The at least one primary sampling sensor may be carried by the first circuit board disposed centrally with respect to the circular array of the emitters.

The sampling system may further include at least one temperature sensor positioned to sense a temperature at least proximate the at least one of the emitters or the at least one primary sampling sensor, and responsive thereto to produce signals indicative of a sensed temperature.

The sampling system may further include at least one control subsystem housed separately from the sampling device, and communicatively coupled to receive sensor information at least from the at least one primary sampling sensor and the at least one calibration sensor.

The at least one control subsystem may be communicatively coupled to control the emitters. The sampling device may further include at least one temperature sensor positioned to sense a temperature at least proximate the at least one of the emitters or the at least one primary sampling sensor, and responsive thereto to provide signals indicative of a sensed temperature to the at least one control subsystem that is housed separately from the sampling device. The at least one control subsystem may calibrate an output value based at least in part on information from both the calibration sensors and the at least one temperature sensor. The at least one control subsystem may calibrate a drive signal supplied to at least one of the emitters based at least in part on information from both the calibration sensors and the at least one temperature sensor. The at least one control subsystem may be a smartphone.

The sampling device may further include at least one control subsystem received in the housing, the at least one control subsystem communicatively coupled to control the emitters, and communicatively coupled to receive sensor information at least from the at least one primary sampling sensor and the at least one calibration sensor.

The sampling device may further include at least one temperature sensor communicatively coupled to the at least one control subsystem, the at least one control subsystem controlling operation based at least in part on information from both the calibration sensors and the at least one temperature sensor.

The at least one temperature sensor may include a plurality of temperature sensors, at least one of the temperature sensors positioned to sense a temperature at least proximate the at least one of the emitters or the at least one primary sampling sensor. The at least one control subsystem may calibrate an output value based at least in part on information from both the calibration sensors and the at least one temperature sensor. The at least one control subsystem may calibrate a drive signal supplied to at least one of the emitters based at least in part on information from both the calibration sensors and the at least one temperature sensor.

The sampling system may further include at least one window that is transmissive to at least some of the wavelengths of electromagnetic energy emitted by the emitters and that provides passage of the wavelengths of electromagnetic energy emitted by the emitters out of an interior of the housing to an exterior of the housing and passage of the wavelengths of electromagnetic energy returned to the sampling device from the exterior of the interior of the housing.

The sampling system may further include a single user manipulable switch, operation of which causes the sampling device to sample a specimen.

The sampling device may automatically provide a signal indicative of information sensed by the primary sampling sensors and the calibration sensors to a remotely housed control subsystem in response to user activation of the user manipulable switch. The respective range of wavelengths of at least two of the emitters may at least partially overlap.

A sampling device operable to sample specimens may be summarized as including a housing having a first end, a second end, and a sampling aperture at least proximate the first end; a plurality of emitters at least partially housed by the housing and arrayed about a first location, the emitters selectively operable to emit electromagnetic energy in respective ranges of wavelengths, the ranges of wavelengths of at least some of the emitters different from the ranges of wavelengths of others of the emitters; at least one annular lens structure at least partially housed by the housing, the at least one annular lens structure positioned with respect to the emitters and the sampling aperture to focus electromagnetic energy emitted by the emitters outwardly from the sampling aperture toward a focal locus; at least one primary sampling sensor at least partially housed by the housing at least proximate the first location and positioned to receive electromagnetic energy returned to the sampling device from a specimen, if any, positioned at the focal locus via the sampling aperture, the at least one primary sampling sensor responsive to at least some of the electromagnetic energy returned to the sampling device via the sampling aperture.

The emitters may be arrayed in a circular array and the at least one annular lens structure may include an annular array of distinct lenses physically coupled to one another. The annular array of distinct lenses may take the form of an integral one-piece construction which includes a circular band that physically couples the distinct lenses to one another. The distinct lenses may each extend radially outwardly from the circular band at an angle with respect to a plane defined by the circular band. The annular array of lenses may include a material that does not distort electromagnetic energy in a near-ultraviolet (N-UV) portion of the electromagnetic spectrum. The at least one annular lens structure may include a high grade optical resin (e.g., cyclic polyolefin). The at least one annular lens structure may include a silica material.

The sampling device may further include a first circuit board on which the emitters are arrayed in a circular array; and an endless array of compartments which isolate each of the emitters from one another.

The endless array of compartments may be formed as a unitary single-piece construction and may be arranged about a central passage. The at least one annular lens structure may include an annular array of distinct lenses physically coupled to one another as an integral one-piece construction which includes a circular band that physically couples the distinct lenses to one another, each of the distinct lenses closely received in a respective one of the compartments of the endless array of compartments. The housing may include a body portion and a lens tube portion that extends from the body portion, the body portion having an interior with an opening, the first circuit board mounted across the opening of the body portion.

The sampling device may further include a second circuit board received in a cavity of the housing, the second circuit board carrying control circuitry communicable coupled to the emitters and at least one primary sampling sensor.

The sampling device may further include a window across the sampling aperture, the window transmissive to at least some wavelengths of electromagnetic energy.

The housing may include a shroud that extends from the lens tube outwardly of the sampling aperture and the window, and which shrouds the sampling aperture and the window.

The sampling device may further include a plurality of calibration sensors, each of the calibration sensors positioned in a respective one of the compartments of the endless array of compartments.

Each compartment may have a slot to limit entrance into the respective compartment of spectral illumination returned to the sampling device from the specimen, if any, and each of the respective calibration sensors may be positioned to be shielded from the respective slot.

The sampling device may further include at least one optical calibration tap that provides a respective distinct optical path between a position at least proximate respective ones of the emitters and respective ones of the calibration sensors.

The at least one optical calibration tap may be an integral portion of the endless array of compartments. The at least one optical calibration tap may be a light-toned polymer insert. The calibration sensors may be matched to the output of the respective emitter with which calibration sensor is compartmentalized. The calibration sensors may each consist of a single optical sensor chip that detects from near-infrared (N-IR) through near-ultraviolet (N-UV) wavelengths of electromagnetic energy. The at least one annular lens structure may focus the electromagnetic energy emitted by the emitters such that the at least one primary sampling sensor receives electromagnetic energy returned to the sampling device from the specimen via Rayleigh scattering, substantially free of electromagnetic energy returned to the sampling device from the specimen via Ramen scattering. The at least one primary sampling sensor may consist of a single optical sensor chip that detects from near-infrared (N-IR) through near-ultraviolet (N-UV) wavelengths of electromagnetic energy. The respective range of wavelengths of at least two of the emitters may at least partially overlap.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 2A is a top isometric view of a transducer printed circuit board (PCB) of the sampling device of FIGS. 1A-1D, which carries a number of transducers, according to another illustrated embodiment.

FIG. 2B is a bottom isometric view of the transducer PCB of the sampling device of FIGS. 1A-1D, according to another illustrated embodiment.

FIG. 2C is a top plan view of the transducer PCB of the sampling device of FIGS. 1A-1D, according to another illustrated embodiment.

FIG. 2D is a bottom plan view of the transducer PCB of the sampling device of FIGS. 1A-1D, according to another illustrated embodiment.

FIG. 2E is a side elevational view of the transducer PCB of the sampling device of FIGS. 1A-1D, according to another illustrated embodiment.

FIG. 2F is a side elevational view of the transducer PCB of the sampling device of FIGS. 1A-1D, according to another illustrated embodiment.

FIG. 5A is a top plan view of a portion of the sampling device of FIGS. 1A-1D illustrating a relative positioning of the various components, according to one illustrated embodiment.

FIG. 5B is a schematic view of a portion of the sampling device of FIGS. 1A-1D illustrating exemplary emitted electromagnetic energy and returned of electromagnetic energy from a sample or specimen, according to one illustrated embodiment.

FIG. 7A is an isometric view of a sampling device with an optional calibration cap coupled to a front thereof, according to one illustrated embodiment.

FIG. 7B is a rear isometric view of the optional calibration cap of FIG. 7A, according to one illustrated embodiment.

DETAILED DESCRIPTION

Figure 1A:
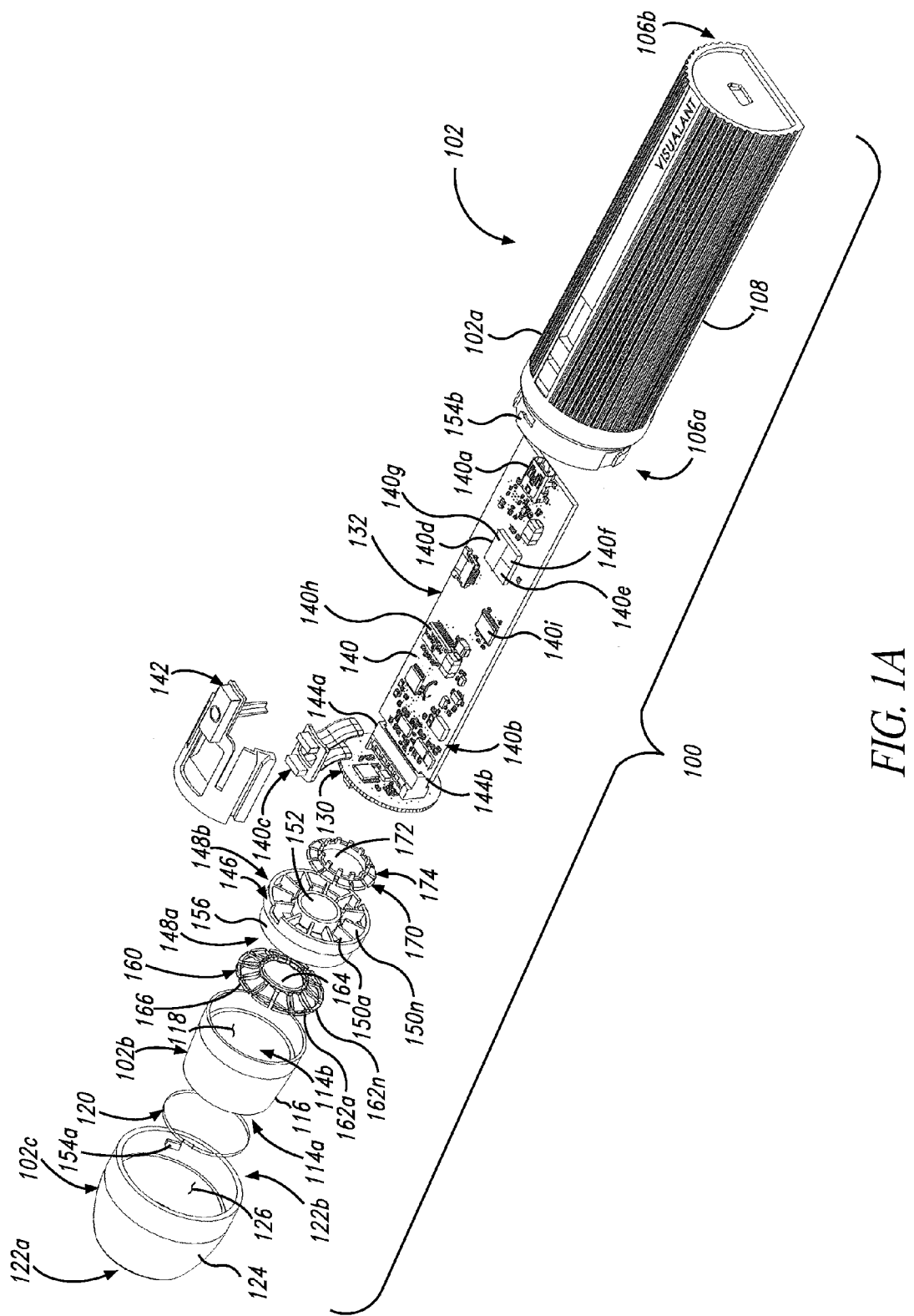
FIG. 1A is an exploded, top, rear, right isometric view of a sampling device according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems, networks, servers, microprocessors, memories, buses, sources of electromagnetic energy, and/or detectors or sensors have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The ability to recognize, identify, verify, authenticate and/or classify objects has numerous commercial applications.

It may be useful to determine analyze characteristics of a sample or specimen being evaluated. For example, it may be useful to determine whether a sample or specimen being evaluated is identical or similar to a previously evaluated sample or specimen, for instance, a reference sample or specimen. Also for example, it may be useful to determine if a sample or specimen is identical to a previously evaluated sample or specimen.

FIGS. 1A-1D show a sample or specimen analysis or evaluation device 100, according to one illustrated embodiment, referred to herein simply as sampling device 100.

As discussed in detail below, the sampling device 100 is operable to sequentially illuminate an object with a number of bands of electromagnetic energy. The sampling device 100 is also operable to detect, measure or otherwise capture electromagnetic energy reflected, emitted, fluoresced, refracted, diffracted or otherwise transmitted, or otherwise returned from the object in response to the illumination. As used herein and in the claims, the terms illuminate, illuminates, illumination, and variations of such terms mean to expose to or reveal by the use of electromagnetic energy or electromagnetic radiation, whether in the visible portion of the electromagnetic spectrum, the optical portion (e.g., visible, near-infrared, near-ultraviolet), or other portions (e.g., far-infrared, far-ultraviolet, microwave, X-ray, etc.).

The sampling device 100 includes a housing 102, which in the illustrated embodiment includes a tubular main housing portion 102a, a lens tube 102b and optionally a shroud 102c.

The main housing portion 102a has a front end 106a and a back end 106b opposite the front end 106a. The main housing portion 102a has a side wall 108 that defines a cavity 110 which is separated from an exterior 112 of the main housing portion 102a. The front end 106a is open to provide selective access to the cavity 110. The main housing portion 102a may be comprised of any of a large variety of materials, for example, ABS plastic, other plastics, metals (e.g., aluminum) and/or composite materials (e.g., carbon fiber impregnated resin). The main body housing portion 102a may be sized and dimensioned to be easily held and operated using a single hand. While illustrated as a cylindrical tube, the main body housing portion 102a may take any variety of shapes.

The lens tube 102b a front end 114a and a back end 114b opposite the front end 114a. The lens tube 102b has a side wall 116 that defines a passage 118 that extends through the front and back ends, 114a, 114b, respectively. The lens tube 102b is physically directly or indirectly coupled via the back end 114b to the front end 106a of the main housing portion 102a, and extends therefrom. The lens tube 102b may, for example, be physically detachably coupled via a press fit or a detent structure (e.g., annular flange and annular slot). The lens tube 102b may be comprised of any of a large variety of materials, for example, ABS plastic, other plastics, metals (e.g., aluminum) and/or composite materials (e.g., carbon fiber impregnated resin), and the side wall 116 is preferably opaque. While illustrated as a fustroconical tube, the lens tube 102b may take any variety of shapes.

As illustrated, the sampling device 100 may include a window or lens cover 120 received in, and across, the open front end 114a of the lens tube 102b. The window or lens cover 120 may provide environmental protection of components within or rearward of the window or lens cover 120. The window or lens cover 120 is transmissive (i.e., transparent or at least translucent) to at least those wavelengths of electromagnetic energy (e.g., UV) which are used in the analysis or evaluation of a sample or specimen. The window or lens cover 120 may be comprised of any of a large variety of materials, for example silica (i.e., fused quartz) or a cyclic polyolefin commercially available from Zeon Chemicals of Louisville, Ky. under the trademark Zeonex®, for example having minimal absorption characteristics for wavelengths between approximately 330 nm and extending to or beyond approximately 1,200 nm.

The shroud 102c has a front end 122a, and a back end 122b opposite the front end 122a. The shroud 102c has a side wall 124 that defines a passage 126 that extends through the front and back ends 122a, 122b, respectively. The shroud 102c is physically coupled via the back end 122b to the front end 114a of the lens tube 102b, and extends therefrom. The shroud 102c may, for example, be physically detachably coupled to the lens tube 102b via a press fit or a detent structure (e.g., annular flange and annular slot). Alternatively or additionally, the shroud 102c may, for example, be physically detachably coupled to the main housing portion 102a via one or more lugs 154a (only one called out in FIGS. 1A, 1B and 1D). The lugs 154a may, for instance, be sized, dimensioned, positioned and/or oriented to be received by slots 154b the on the main housing portion 102a. The shroud 102c may be comprised of any of a large variety of materials, for example, ABS plastic, other plastics, metals (e.g., aluminum) and/or composite materials (e.g., carbon fiber impregnated resin), and the side wall 124 is preferably opaque. While illustrated as a generally conical or body of revolution shape, the shroud 102c may take any variety of shapes.

In the illustrated embodiment, the sampling device 100 includes a transducer printed circuit board (PCB) 130 and a controller PCB 132. As explained in more detail below, the transducer PCB 130 includes a plurality of transducers, typically in the form of a plurality of emitters (collectively 134), one or more primary detectors or sensors (collectively 136), and one or more calibration detectors or sensors (collectively 138). Also as explained in more detail below, the controller PCB 132 includes various components electrical and electronic components (collectively 140) to control operation of the sampling device 100 and/or communications therefrom. The transducer PCB 130 and the controller PCB 132 each include a respective coupler or connector 144a, 144b, respectively, to communicatively couple components or circuits of the transducer PCB 130 with the components or circuits of the controller PCB 132.

The controller PCB 132 may, for example, include one or more communications ports 140a (e.g., Universal Serial Bus compliant socket or female connector). The communications port(s) 140a may be accessible from the exterior of the housing 102, for example, via an aperture (not shown) in the back end 106b of the main housing portion 102a. While illustrated as a hardwired communication port 140a (e.g., a USB port), the sampling device 100 may include other types of communications ports or devices, for instance, an infrared transceiver, or an RF transceiver (e.g., BLUETOOTH® transceiver). Such may allow the transmission of data, instructions and/or results, to or from the sampling device 100. Such communications may be via one or more converters, for example a USB to serial converter 140m.

The controller PCB 132 may, for example, include one or more visual indicators (e.g., light emitting diodes or LEDs, two shown collectively referenced as 140b). The visual indicators 140b may indicate a status or mode of the sampling device, for instance via different colors (e.g., green, red, amber) and or patterns (e.g., flashes). One or more light communicative paths 140c (e.g., optical fiber or light pipes) may communicatively coupled light from the visual indicators 140b to an exterior of the main housing portion 106a. Alternatively, one or more visual indicators 140b may be carried by or on the main housing portion 106a, or underlying a window (not shown) in the main housing portion 106a.

Figure 1B:
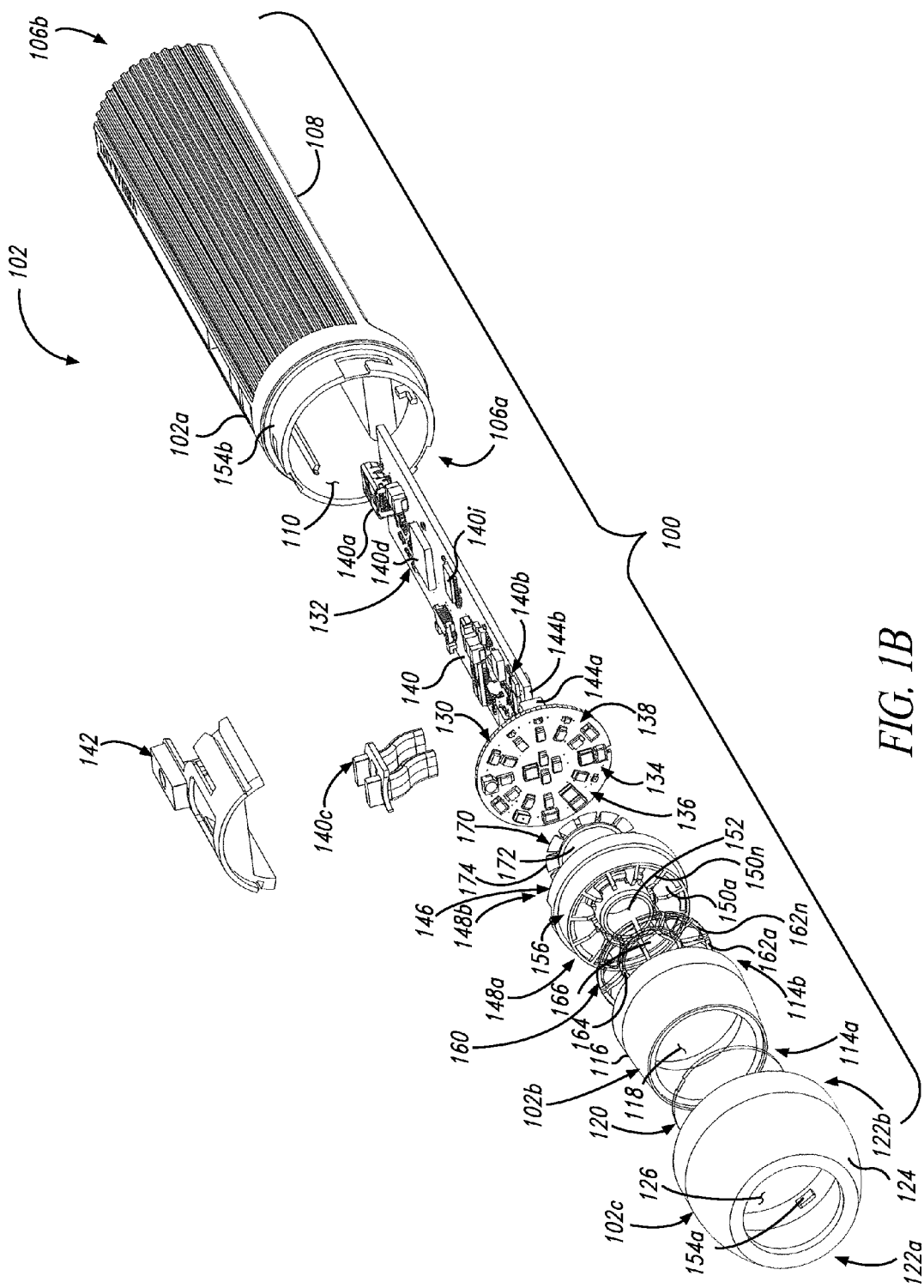
FIG. 1B is an exploded, top, front, right isometric of a sampling device according to one illustrated embodiment.
Figure 1C:
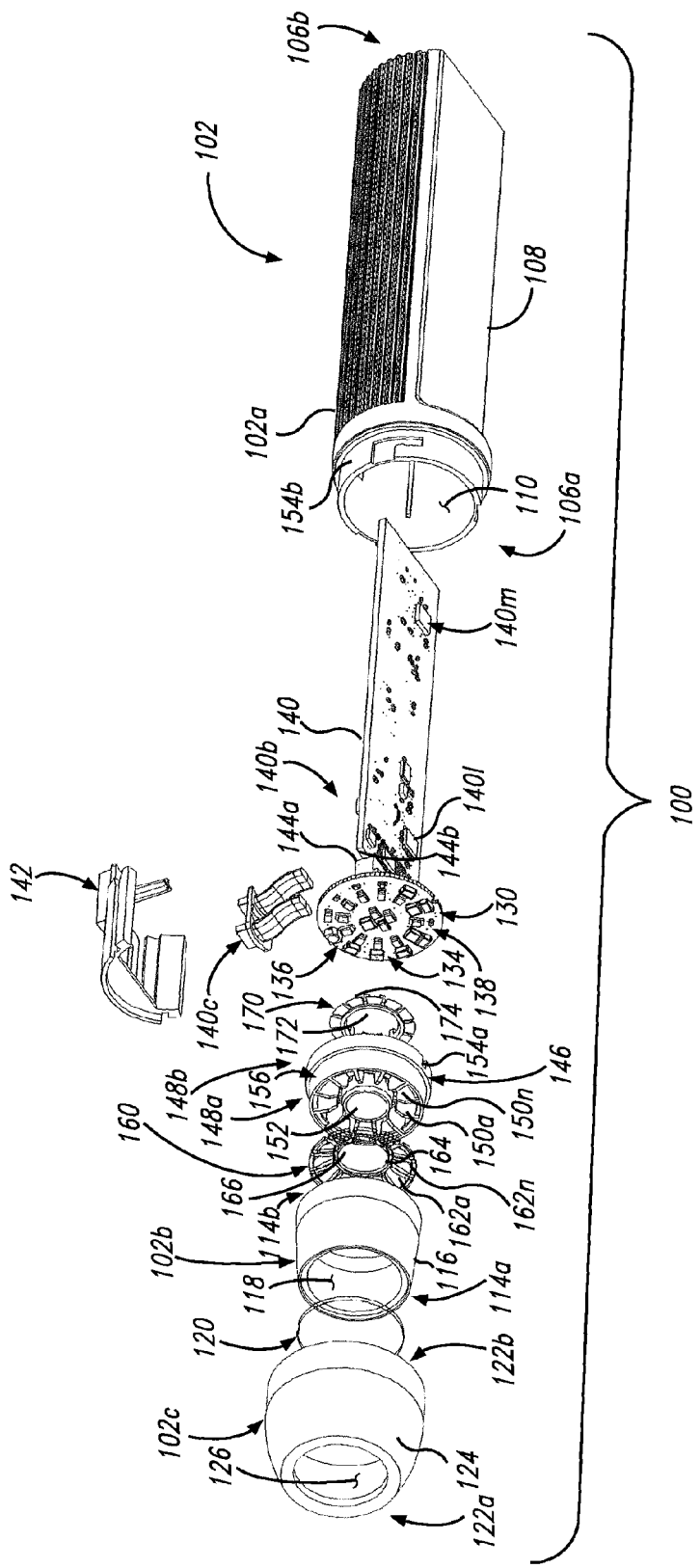
FIG. 1C is an exploded, bottom, front, right isometric view of a sampling device according to one illustrated embodiment.
Figure 1D:
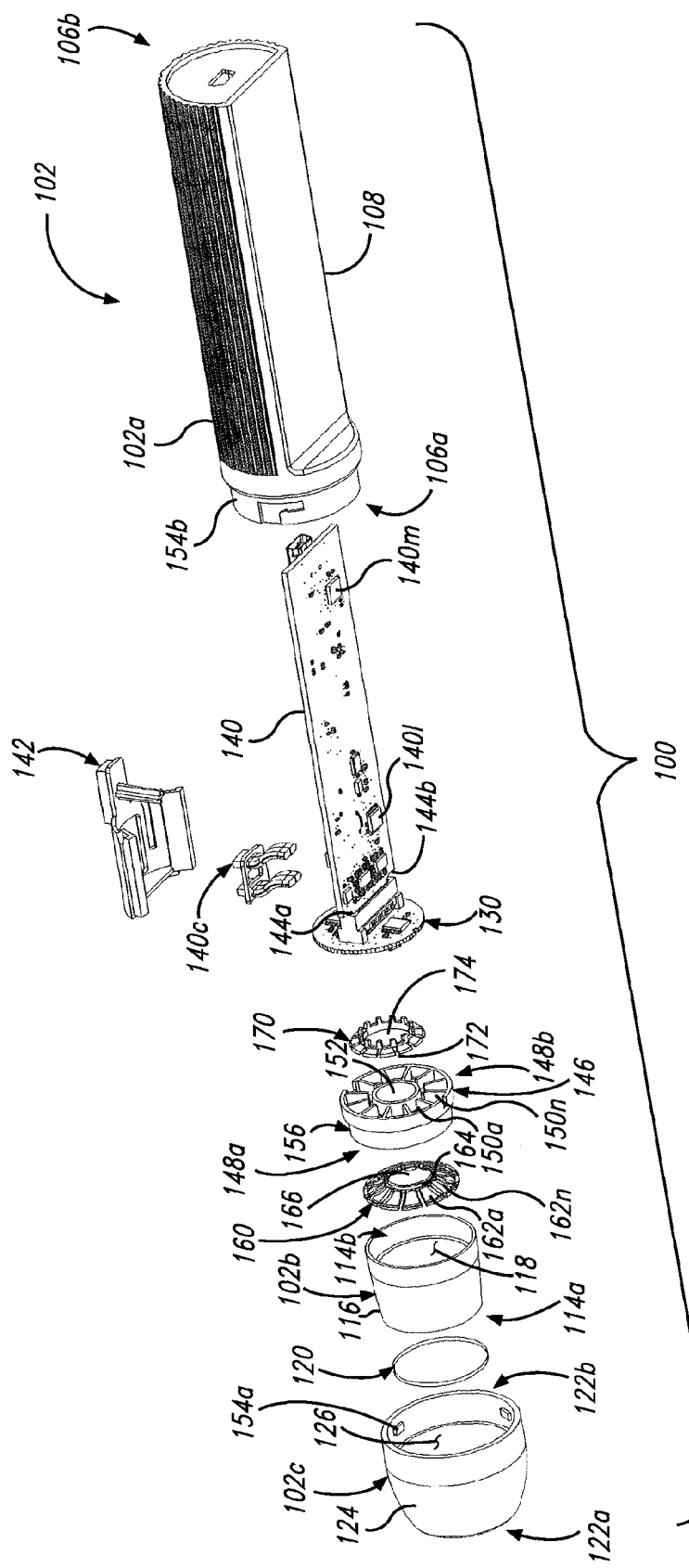
FIG. 1D is an exploded, bottom, rear, right isometric view of a sampling device according to one illustrated embodiment.
Figure 1E:
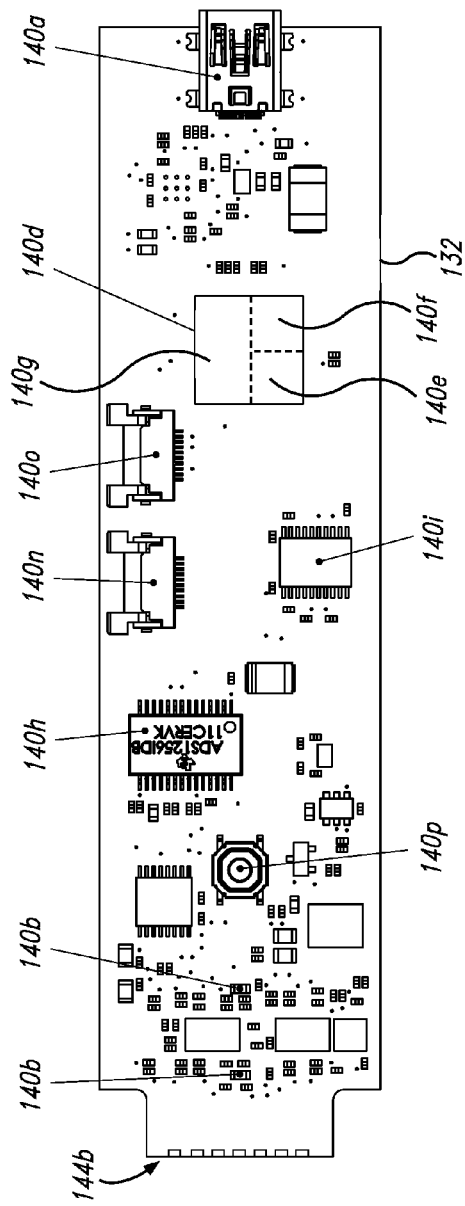
FIG. 1E is a top plan view of a controller printed circuit board for use in the sampling device of FIGS. 1A-1D, according to one illustrated embodiment.
Figure 1F:
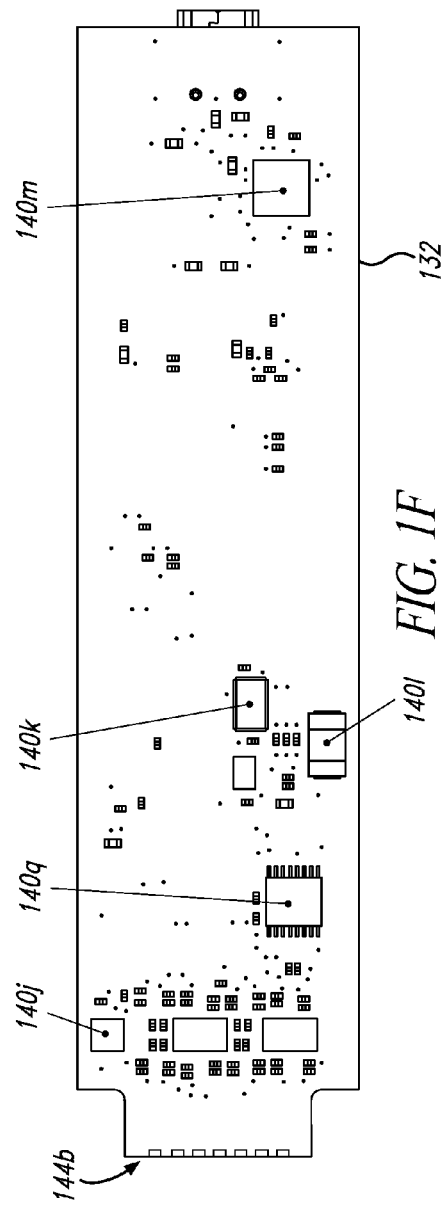
FIG. 1F is a bottom plan view of the controller printed circuit board for use in the sampling device of FIGS. 1A-1D, according to one illustrated embodiment.

The controller PCB 132 may, for example, optionally include a control subsystem, some portions of which are best illustrated in FIGS. 1E and 1F. Alternatively, the sampling device may be coupled to an external control system, for example, one or more programmed general purpose or special purpose computers or computer systems.

The control subsystem may include one or more controllers 140d. The controller 140d may, for example, take the form of an integrated circuit package that includes one or more microprocessors, digital signal processors (DSPs), application specific integrated circuits (ASICs), programmable gate arrays (PGA), programmable logic controllers (PLCs), or other logic executing device, denominated herein as a central processing unit 140g. The control subsystem may include one or more non-transitory computer- or processor-readable media, for example, one or more memories such as read only memory (ROM) or Flash memory 140e and random access memory (RAM) 140f. While the ROM or Flash memory 140e and RAM 140f are shown integrated into the same integrated circuit (ICs) package 140d as the CPU 140g, such can be supplied as discrete ICs. One or more buses (not shown) may couple the ROM 140e and RAM 140f to the controller 140d. The buses may take a variety of forms including an instruction bus, data bus, other communications bus and/or power bus. The nonvolatile ROM and/or Flash memory 140e may store instructions and/or data for controlling the sampling device 100. The volatile RAM 140f may store instructions and/or data for use during operation of the sampling device 100.

The controller PCB 132 may, for example, include an analog-to-digital converter 140h, communicatively coupled to convert analog signals, for instance from the sensor, to digital signals for use by the CPU 140g. The controller PCB 132 may, for example, include a level translator 140i coupled to translate signal levels. The controller PCB 132 may, for example, include a current source 140j, to supply a constant current to the other components 140 for instance the LEDs 140b. The controller PCB 132 may, for example, include an oscillator or clock, for instance a crystal oscillator 140k, communicatively coupled to the controller 140d to provide a clock signal thereto. The controller PCB 132 may, for example, include one or more capacitors, for instance a tantalum capacitor 140l.

The optional controller 140d employs instructions and or data from the ROM/Flash 140e and RAM 140f in controlling operation of the sampling device 100. For example, the controller 140d operates the emitters 134 in one or more sequences. The sequences determine an order in which the emitters 134 are turned ON and OFF. The sequences may also indicate an ordered pattern of drive levels (e.g., current levels, voltage levels, duty cycles) for the emitters 134. Thus, for example, a controller 140d may cause the application of different drive levels to respective ones of the emitters 134 to cause the emitters 134 to emit in distinct bands of the electromagnetic spectrum. The controller 140d may process information generated by the primary detector(s) or sensor(s) 136, which is indicative of the response by at least a portion of a sample or specimen to illumination by the emitters 134. The information at any given time may be indicative of the response by the sample or specimen to illumination by one or more of the emitters 134. Thus, the information over a period of time may be indicative of the responses by the sample or specimen to sequential illumination by each of a plurality of the emitters 134, where each of the emission spectra of each of the emitters 134 has a different center, bandwidth and/or other more complex differences in spectral content, such as those described above (e.g., the width of the band, the skew of the distribution, the kurtosis, etc.).

The control subsystem may optionally include a buffer (not shown) to buffer information received from the primary detector or sensors 136. The control subsystem may further optionally include an analog to digital converter (ADC) (not shown) and/or digital to analog converter (DAC) (not shown). An ADC may, for example, be used for converting analog photodiode responses into digital data for further analysis and/or transmission. A DAC may, for example, be used for converting digital computer or controller commands into analog LED current levels. The control subsystem may additionally or alternatively optionally include an analog signal processor, which may be particularly useful where the sensor takes the form of one or more photodiodes.

The control subsystem may include a user interface including one or more user interface devices. For example, the control subsystem 54 may include one or more speakers or microphones (not shown). Also for example, the control subsystem may include and/or one or more visual indicators, such as one or more LEDs 140b, liquid crystal displays (LCD), or other visual indicator. The LCD may, for example, take the form of a touch sensitive LCD, which displays a graphical user interface, operable by the user of the sampling device 100. Additionally, or alternatively, the control subsystem may include one or more user operable input elements, such as switches, keys or buttons 142. The input elements may include a switch 142 for turning the sampling device 100 ON and OFF. Additionally, or alternatively, the input elements may include one or more switches or keys for controlling the operation of the test device 100, for example, downloading or uploading data or instructions to or from the sampling device 100. Such may be via one or more connectors, for instance a debug connector 140n and a programming connector 140o, both positioned to be accessible from an exterior of the sampling device 100.

The sampling device 100 may include one or more switches 142 which are operable from an exterior of the sampling device 100. The switch 142 may take any of a large variety of forms. For example a contact or slideable switch 142 may be actuatable via a window, slot or other aperture in the main housing portion 102a. Alternatively, a touch sensitive switch may be employed, for instance, an inductive or a capacitive switch. The switch 142 may be responsive to actuation to send a signal, for instance via a tactile switch 140p and/or analog switch 140q, or otherwise cause the sampling device 100 to execute a sampling operation. As discussed in detail below, the sampling operation may be preceded by a calibration operation.

The sampling device 100 may optionally include a power source (not shown). The power source may take the form of a portable power source, for example, one or more batteries, fuel cells, and/or super- or ultra-capacitors. Additionally, or alternatively, the power source may take the form of a fixed power source, such as a cable plugged into a port of a computer (e.g., USB cable) or a conventional electrical receptacle (e.g., wall outlet).

As illustrated, the controller PCB 132 may be received in the cavity 110 of the main housing portion 102a. In particular, the controller PCB 132 may be sized and dimensioned to be securely received in the cavity 110, for example, engaging an inner periphery of the side wall 108 or other attachment structures in the cavity 110. Engagement may be via a press fit or via some coupling structure such as a detent structure.

As illustrated, the transducer PCB 130 may be physically coupled across the otherwise open front end 106a of the main housing portion 102a. As visible in FIGS. 1A, 1B, 1D, the transducer PCB 130 may include the coupler or connector 144a, for instance, a slot connector having a slot sized and dimensioned to receive the coupler of connector 144b of the controller PCB 132, for instance, an edge or tab. Each of the couplers or connectors 144a, 144b typically carry a variety of electrical contacts, although other signal transfer structures (e.g., optical fiber) can be employed.

The sampling device 100 includes a compartment structure 146, having a front end 148a and a back end 148b opposite the front end 148a, and which includes an endless array of compartments 150a, 150n (collectively 150, twelve shown, only two called out in FIGS. 1A-1D). The compartments 150 are each open at the front end 148a and the back end 148b. The compartment structure 146 may be annular and may include a central passage 152 extending between the front and back ends 148a, 148b, respectively. The compartment structure 146 may comprise any of a large variety of materials, for example, plastics or even metals or composite materials. The compartment structure 146 is typically opaque or a substantial portion thereof is opaque, at least to electromagnetic energy that is employed in the analysis or evaluation of the samples or specimens. The compartment structure 146 may, for example, be painted black, coated black, or may include black pigments.

The compartment structure 146 is physically coupled to the main housing portion 102a. In particular, the compartment structure 146 may be physically detachably coupled to the main housing portion 102a. For example, the compartment structure 146 may include a portion of a bayonet or other physical coupler structure which physically couples to the physical coupler structure of the main housing portion 102a. For instance, the compartment structure 146 may include a set of slots 154b (e.g., L-shaped slots) defined in a perimeter proximate the front end 106a of the main housing portion 102a. The 154b (e.g., L-shaped slots) may be sized, dimensioned, positioned, and/or oriented to securely releasably receive a set of lugs 154a. While illustrated as carried by the shroud 102c, the lugs 154a could be carried by some other component, for instance the lens tube 102b. Such secures the various components in place, including the compartment structure 146, yet still allows easy and fast access to various internal components (e.g., transducer PCB 130, controller PCB 132). The compartment structure 146 may include an annular rim portion 156, sized and dimensioned to be securely received by the passage 118 of the lens tube 102b, via the back end thereof, for instance, via a press fit.

When mounted in front of the transducer PCB 130, each compartment 150 serves as a mask, separating sets of one or more emitters 134 from other sets of one or more emitters 134 on the transducer PCB 130. The compartments 150 also separate sets of one or more calibration detectors or sensors 138 from other sets of one or more calibration detectors or sensors 138 on the transducer PCB 130. In particular, each compartment 150 may house a respective set of emitters 134 with a respective set of calibration detectors or sensors 138. The compartments 150 may also limit an amount of electromagnetic energy which may leak into the compartment 150 from outside of the compartment 150, for example, light being returned from a sample or specimen. The central passage 152 allows electromagnetic energy to reach the primary detectors or sensors 136. The central passage 152 allows electromagnetic energy returned from a sample or specimen to reach the primary detectors or sensors 136.

The sampling device 100 includes an annular lens element 160. The annular lens element 160 may include a number of distinct lenses 162a, 162n (collectively 162, twelve shown, only two called out in FIGS. 1A-1D). The distinct lenses 162 may be physically coupled by a band 164 (shown more clearly in FIGS. 3A and 3B), on an inner diameter 166 of the annular lens element 160. Each lens 162 is sized and dimensioned to be received by, or across, a respective one of the compartments 150 of the mask structure 146. The lenses 162 are distributed about the band 164 to match the arrangement of compartments 150. Coupling or connecting all the distinct lenses with the band 164 allows all lenses 162 to be easily handled, facilitating manufacturing operation and/or maintenance. At least the distinct lenses 162 should be transmissive of wavelengths of electromagnetic energy (e.g., UV) which will be emitted by the emitters for use in the analysis or evaluation of a sample or specimen. Thus, the lenses 162, and optionally the band 164, may be comprised of any of a large variety of materials, for example, silica (i.e., fused quartz) or a cyclic polyolefin commercially available from Zeon Chemicals of Louisville, Ky. under the trademark Zeonex®, for example, having minimal absorption characteristics for wavelengths between approximately 330 nm and extending to or beyond approximately 1,200 nm.

The sampling device 100 may optionally include a calibration tap. The calibration tap provides a respective path to respective sets of calibration sensors 138 for electromagnetic energy emitted by emitters 134, and may take any of a variety of forms.

In the illustrated embodiment, calibration tap takes the form of a light-toned polymer insert generally indicated at 170. The insert 170 may be generally annular having a central passage 172. The insert 170 may have a plurality of segments 174 (collectively 174, twelve shown, only one called out in FIGS. 1A-1D). The segments 174 correspond in number of position to the compartments 150 of the compartment structure 148, and are sized and dimensioned to be received by respective ones of the compartments 150. This allows the compartment structure 150 to, for example, be matte black, while still ensuring that electromagnetic energy emitted by an emitter is received by a respective calibration sensor 138. As illustrated, the insert 170 may take the form of a unitary one-piece element.

The calibration tap may take the form of a band of a known color, for example, a band of a light-tone or white color having a defined or known affect on light reflected or scattered by the band of color. The band may, for example, be carried on an inner annular surface of the compartment structure, for example, being an integral portion of the compartment structure 146.

Alternatively, the calibration tap may take the form of a pipe which is transmissive of wavelengths of electromagnetic energy (e.g., UV) which will be emitted by the emitters for use in the analysis or evaluation of a sample or specimen. Thus, the calibration tap may be comprised of any of a large variety of materials, for example, silica (i.e., fused quartz) or a cyclic polyolefin commercially available from Zeon Chemicals of Louisville, Ky. under the trademark Zeonex®.

Table A, below, provides a list of suitable parts for the controller PCB 132. Such is purely illustrative and is not intended to require any specific parts.

TABLE A

| ITEM No. | PART No. | DESCRIPTION | QTY. |
|---|---|---|---|
| 140b | APT1608QBC-D BLUE | LED | 2 |
| 140h | AD1256 | ANALOG - DIGITAL CONVERTER | 1 |
| 140n 140o | FH12A-10S-0.5SH (55) | DEBUG & PROG CONNECTOR | 2 |
| 140p | SKQGAB | TACTILE SWITCH | 1 |
| 140i | ST2378ETTR | LEVEL TRANSLATOR | 1 |
| 140d | R5F52108AGFM | CPU | 1 |
| 132 | PCB | CONTROLLER PCB | 1 |
| 140a | MU-10F4-08 | 10 WAY USB SOCKET MU-10F4-08 | 1 |
| 140j | LT3092XDD | CURRENT SOURCE | 1 |
| 140q | ADG728BRUZ | ANALOGUE SWITCH | 1 |
| 140k | 7B-8.000MAAJ-T | 8 MHz CRYSTAL | 1 |
| 140l | 47Uf 16V | TANTALUM CAPACITOR | 1 |
| 140m | FT232RQ | USB TO SERIAL CONVERTER | 1 |

FIGS. 2A-2E show the transducer PCB 130 of FIGS. 1A-1D in more detail.

As is best illustrated in FIGS. 2A and 2C, the transducer PCB 130 carries a number of sets of emitters or sources 134a-134l (twelve shown, individually called out in FIG. 2C, collectively 134) arrayed along an outer perimeter 200 of the transducer PCB 130 about a central portion 202 of the transducer PCB 130. The sets of emitters or sources 134 may, for example, be arrayed in a generally annular array, as illustrated. Each respective set may include one or more emitters, although typically each set will have a single emitter 134. Alternatively, each set may include multiple emitters, the emitters of any given set emitting at the same band of wavelengths. Optionally, some sets may include multiple emitters, the emitters of the set emitting at different bands of wavelengths.

The emitters 134 may take a variety of forms which are operable to emit electromagnetic energy. The emitters 134 may, for example, take the form of one or more light emitting diodes (LEDs), including, for instance, organic LEDs (OLEDs). Alternatively, or additionally, the emitters 134 may take the form of one or more lasers, for example, one or more laser diodes. The lasers may, or may not, be tunable lasers.

Alternatively, or additionally, the emitters 134 may take the form of one or more incandescent sources such as conventional or halogen light bulbs.

One, more or all of the emitters 134 may be operable to emit in part or all of an "optical" portion of the electromagnetic spectrum, including the (human) visible portion, near infrared (N-IR) portion and/or or near ultraviolet (N-UV) portion of the electromagnetic spectrum. Additionally, or alternatively, the emitters 134 may be operable to emit electromagnetic energy of other portions of the electromagnetic spectrum, for example, the infrared, ultraviolet and/or microwave portions.

In some embodiments, at least some of the emitters 134 are operable to emit in or at a different band than other of the emitters 134. For example, one or more emitters 134 may emit in a band centered around 450 nm, while one or more of the emitters 134 may emit in a band centered around 500 nm, while a further emitter or emitters 134 may emit in a band centered around 550 nm. In some embodiments, each emitter 134 emits in a band centered around a respective frequency or wavelength, different than each of the other emitters 134. Using emitters 134 with different band centers advantageously maximizes the number of distinct samples that may be captured from a fixed number of emitters 134. This may be particularly advantageous where the sampling device 100 is relatively small, and has limited space or footprint for the emitters 134.

The distribution of spectral content for each emitter 134 may vary as a function of drive level (e.g., current, voltage, duty cycle), temperature, and other environmental factors, depending on the specific emitter 134. Such variation may be advantageously actively employed to operate one or more of the physical emitters or sources 134 as a plurality of "logical emitters or sources," each of the logical emitters or sources operable to provide a respective emission spectra from a respective physical emitter or source 134. Thus, for example, the center of the band of emission for each emitter or source 134 may vary according to a drive level and/or temperature. For example, the center of the band of emission for LEDs will vary with drive current or temperature. One way the spectral content can vary is that the peak wavelength can shift. However, the width of the band, the skew of the distribution, the kurtosis, etc., can also vary. Such variations may also be advantageously employed to operate the physical emitters or sources 134 as a plurality of logical emitters or sources. Thus, even if the peak wavelength were to remain constant, the changes in bandwidth, skew, kurtosis, and any other change in the spectrum can provide useful variations in the operation of the sampling device 100. Likewise, the center of the band of emission may be varied for tunable lasers. Varying the center of emission bands for one or more emitters 134 advantageously maximizes the number of samples that may be captured from a fixed number of emitters 134. Again, this may be particularly advantageous where the sampling device 100 is relatively small, and has limited space or footprint for the emitters 134.

As is best illustrated in FIGS. 2A and 2C, the transducer PCB 130 carries a number of primary detectors or sensors 136a-136d (four shown, collectively 136) positioned in the central portion 202 with respect to the array of emitters or sources 134. The primary detectors or sensors 136 may, for example, include two more sensors or detectors, each responsive to a respective band of wavelengths. Such bands may be mutually exclusive or may be overlapping. The illustrated embodiment employs four primary detectors or sensors 136a-136d, each responsive to a respective band of wavelengths (i.e., 400 nm-1100 nm, 400 nm-1050 nm, 400 nm-1050 nm, 600 nm-1700 nm, respectively). Three primary detectors or sensors 136a-136c that are responsive to N-UV wavelengths are employed to increase sensitivity. Another embodiment employs one or more wideband primary detectors or sensors 136. For example, a pyroelectric detector from Pyreos Ltd. Optionally, one or more filters (not shown) may be employed with the primary detectors or sensors 136, for example, one or more low pass filters, high pass filters, and/or band pass filters. The filters may be optical filters and may be formed or carried directly on the primary detectors or sensors 136. Alternatively, the filters may be formed on or carried on another surface, in the field of view of but spaced from the primary detectors or sensors 136.

The primary detector(s) or sensor(s) 136 can take a variety of forms suitable for sensing or responding to electromagnetic energy. For example, the primary detector(s) or sensor(s) 136 may take the form of one or more photodiodes (e.g., germanium photodiodes, silicon photodiodes). Alternatively, or additionally, the primary detector(s) or sensor(s) 136 may take the form of one or more photomultiplier tubes. Alternatively, or additionally, the primary detector(s) or sensor(s) 136 may take the form of one or more CMOS image sensors. Alternatively, or additionally, the primary detector(s) or sensor(s) 136 may take the form of one or more charge coupled devices (CCDs). Alternatively, or additionally, the primary detector(s) or sensor(s) 136 may take the form of one or more micro-channel plates. Other forms of electromagnetic sensors may be employed, which are suitable to detect the wavelengths expected to be returned in response to the particular illumination and properties of the object being illuminated.

The primary detector(s) or sensor(s) 136 may be formed as individual elements, one-dimensional array of elements and/or two-dimensional array of elements. For example, the primary detector(s) or sensor(s) 136 may be formed by one germanium photodiode and one silicon photodiode, each having differing spectral sensitivities. The test device 14 may employ a number of photodiodes with identical spectral sensitivities, with different colored filters (e.g., gel filters, dichroic filters, thin-film filters, etc.) over the photodiodes to change their spectral sensitivity. This may provide a simple, low-cost approach for creating a set of sensors with different spectral sensitivities, particularly since germanium photodiodes are currently significantly more expensive that silicon photodiodes. Also, for example, the primary detector(s) or sensor(s) 136 may be formed from one CCD array (one-dimensional or two-dimensional) and one or more photodiodes (e.g., germanium photodiodes and/or silicon photodiodes). For example, the primary detector(s) or sensor(s) 136 may be formed as a one- or two-dimensional array of photodiodes. A two-dimensional array of photodiodes enables very fast capture rate (i.e., camera speed) and may be particularly suited for use in assembly lines or high speed sorting operations. For example, the primary detector(s) or sensor(s) 136 may be formed as a one- or two-dimensional array of photomultipliers. Combinations of the above elements may also be employed.

In some embodiments, the primary detector(s) or sensor(s) 136 may be a broadband sensor sensitive or responsive over a broad band of wavelengths of electromagnetic energy. In some embodiments, the primary detector(s) or sensor(s) 136 may be a narrowband sensor sensitive or responsive over a narrow band of wavelengths of electromagnetic energy. In some embodiments, the primary detector(s) or sensor(s) 136 may take the form of several sensor elements, as least some of the sensor elements sensitive or responsive to one narrow band of wavelengths, while other sensor elements are sensitive or responsive to a different narrow band of wavelengths.

This approach may advantageously increase the number of samples that may be acquired using a fixed number of sources. In such embodiments the narrow bands may, or may not, overlap.

As is best illustrated in FIGS. 2A and 2C, the transducer PCB 130 carries a number of calibration detectors or sensors 138a-138l (twelve shown, collective 138), arrayed along the outer perimeter of the transducer PCB 130, for example, radially inwardly from emitters 134. Typically, the number of calibration detectors or sensors 138 will correspond to the number of sets of emitters 134. The calibration detectors or sensors 138 are generally radially aligned with respective emitters 134, the calibration detectors or sensors 138 and emitters 134, for example, being arranged in radial segments on a surface of the transducer PCB 130. The calibration detectors or sensors 138 may match a nominal output of the respective emitter 134 to which the calibration detectors or sensors 138 is paired or segmented. Thus, some of the calibration detectors or sensors 138 may be responsive to different respective bands of wavelengths than the others. Such bands may be mutually exclusive or may be overlapping. In some embodiments, one or more wideband calibration detectors or sensors 138 are, for example, a pyroelectric detector from Pyreos Ltd. Such may advantageously reduce parts counts, while still allowing calibration across the range of wavelengths of the emitters 136. Optionally, one or more filters (not shown) may be employed with the calibration detectors or sensors 138, for example, one or more low pass filters, high pass filters, and/or band pass filters. The filters may be optical filters and may be formed on or carried directly on the calibration detectors or sensors 138. Alternatively, the filters may be formed on or carried on another surface, in the field of view of, but spaced from, the calibration detectors or sensors 138.

The calibration detector(s) or sensor(s) 138 can take a variety of forms suitable for sensing or responding to electromagnetic energy. For example, the calibration detector(s) or sensor(s) 138 may take the form of one or more photodiodes (e.g., germanium photodiodes, silicon photodiodes). Alternatively, or additionally, the calibration detector(s) or sensor(s) 138 may take the form of one or more photomultiplier tubes. Alternatively, or additionally, the calibration detector(s) or sensor(s) 138 may take the form of one or more CMOS image sensors. Alternatively, or additionally, the calibration detector(s) or sensor(s) 138 may take the form of one or more charge coupled devices (CCDs). Alternatively, or additionally, the calibration detector(s) or sensor(s) 138 may take the form of one or more micro-channel plates. Other forms of electromagnetic sensors may be employed, which are suitable to detect the wavelengths expected to be returned in response to the particular illumination and properties of the object being illuminated.

The calibration detector(s) or sensor(s) 138 may be formed as individual elements, one-dimensional array of elements and/or two-dimensional array of elements. For example, the calibration detector(s) or sensor(s) 138 may be formed by one germanium photodiode and one silicon photodiode, each having differing spectral sensitivities. The test device 14 may employ a number of photodiodes with identical spectral sensitivities, with different colored filters (e.g., gel filters, dichroic filters, thin-film filters, etc.) over the photodiodes to change their spectral sensitivity. This may provide a simple, low-cost approach for creating a set of sensors with different spectral sensitivities, particularly since germanium photodiodes are currently significantly more expensive that silicon photodiodes. Also, for example, the calibration detector(s) or sensor(s) 138 may be formed from one CCD array (one-dimensional or two-dimensional) and one or more photodiodes (e.g., germanium photodiodes and/or silicon photodiodes). For example, the calibration detector(s) or sensor(s) 138 may be formed as a one- or two-dimensional array of photodiodes. A two-dimensional array of photodiodes enables very fast capture rate (i.e., camera speed) and may be particularly suited for use in assembly lines or high speed sorting operations. For example, the calibration detector(s) or sensor(s) 138 may be formed as a one- or two-dimensional array of photomultipliers. Combinations of the above elements may also be employed.

In some embodiments, the calibration detector(s) or sensor(s) 138 may be a broadband sensor sensitive or responsive over a broad band of wavelengths of electromagnetic energy. In some embodiments, the calibration detector(s) or sensor(s) 138 may be a narrowband sensor sensitive or responsive over a narrow band of wavelengths of electromagnetic energy. In some embodiments, the calibration detector(s) or sensor(s) 138 may take the form of several sensor elements, as least some of the sensor elements sensitive or responsive to one narrow band of wavelengths, while other sensor elements are sensitive or responsive to a different narrow band of wavelengths. This approach may advantageously increase the number of samples that may be acquired using a fixed number of sources. In such embodiments the narrow bands may, or may not, overlap.

As best illustrated in FIGS. 2B, 2D, and 2E the transducer PCB 130 carries a coupler or connector 144a to make communicative connection to the controller PCB 132 (FIGS. 1A, 1B).

Also as best illustrated in FIGS. 2B, 2D, and 2E the transducer PCB carries a number of thermal sensors 204a-204d (four shown, collectively 204). The thermal sensors 204 are distributed to detect temperatures at a variety of points or locations. Such temperatures may be indicative of temperatures to which the emitters 134, primary detectors or sensors 136 and/or calibration detectors or sensors 138, are subjected. Temperature indicative signals from the thermal sensors may be employed in calibration, for example, calibrating results or responses and/or calibrating drive signals to account for variation from nominal temperatures or other conditions.

Table B, below, provides a list of suitable parts for the transducer PCB 130. Such is purely illustrative and is not intended to require any specific parts, specific wavelengths, or sensitivities.

TABLE B

| Ref. No. | Part No. | Description | Default/Qty. |
| --- | --- | --- | --- |
| 130 | Max2 Sensor PCB | PCB | 1 |
| 204a-204d | MCP98242 | Thermal Sensor | 4 |
| 144a | HSEC8-120-01-X-DV | Connector | 1 |
| 134a | 350-PLCC2-120 | 352 nm | 1 |
| 134b | SM1206UV-395-IL | 400 nm | 1 |
| 134c | EL-19-21/BHC-AN1P2/3T | 468 nm | 1 |
| 134d | PG1112C-TR | 567 nm | 1 |
| 134e | LTST-C190KYKT | 595 nm | 1 |
| 134f | SMC810 | 810 nm | 1 |
| 134g | SMC1200 | 1200 nm | 1 |
| 134h | LNJ812R83RA | 630 nm | 1 |
| 134i | SMC1450 | 1450 nm | 1 |
| 134j | SMC910 | 910 nm | 1 |
| 134k | LN1251CTR | 700 nm | 1 |
| 134l | SMC970 | 970 nm | 1 |
| 138a | SFH2701 | 400-1050 nm | 1 |
| 138b | SFH2701 | 400-1050 nm | 1 |
| 138c | PDB-C152SM | 400-1100 nm | 1 |
| 138d | PDB-C152SM | 400-1100 nm | 1 |
| 138e | PDB-C152SM | 400-1100 nm | 1 |

TABLE B-continued

| Ref. No. | Part No. | Description | Default/Qty. |
|---|---|---|---|
| 138f | PDB-C152SM | 400-1100 nm | 1 |
| 138g | LAPD-1-06-17-LCC | 600-1700 nm | 1 |
| 138h | PDB-C152SM | 400-1100 nm | 1 |
| 138i | LAPD-1-06-17-LCC | 600-1700 nm | 1 |
| 138j | PDB-C152SM | 400-1100 nm | 1 |
| 138k | PDB-C152SM | 400-1100 nm | 1 |
| 138l | PDB-C152SM | 400-1100 nm | 1 |
| 136a | PDB-C152SM | 400-1100 nm | 1 |
| 136b | SFH2701 | 400-1050 nm | 1 |
| 136c | PDB-C152SM | 400-1100 nm | 1 |
| 136d | LAPD-1-06-17-LCC | 600-1700 nm | 1 |

Figure 3A:
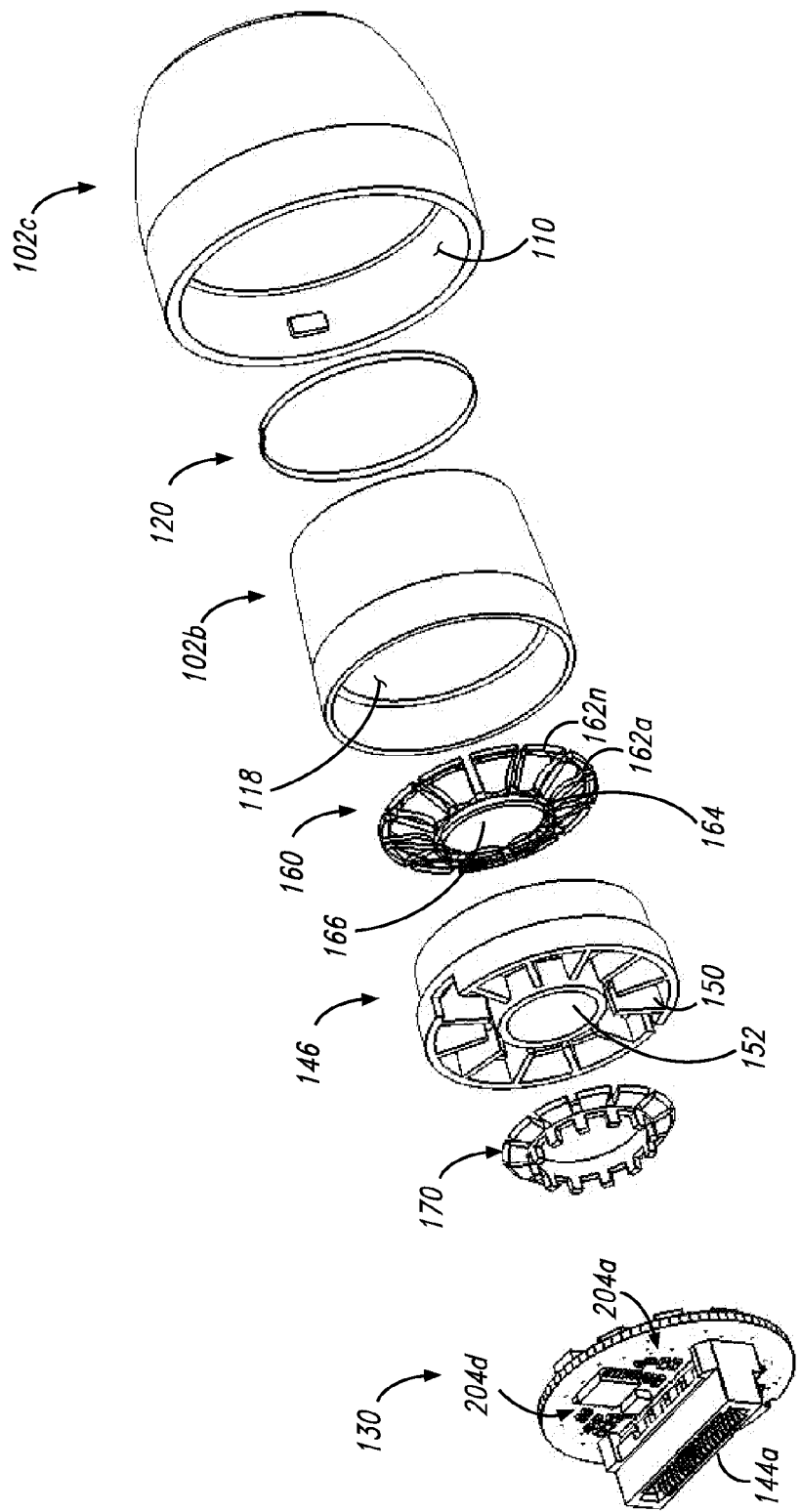
FIG. 3A is a partial exploded rear, left side isometric view of the sampling device of FIGS. 1A-1D, according to another illustrated embodiment, showing the transducer PCB, light pipe, array of compartments, annular lens structure, tube, window and operational shroud.
Figure 3B:
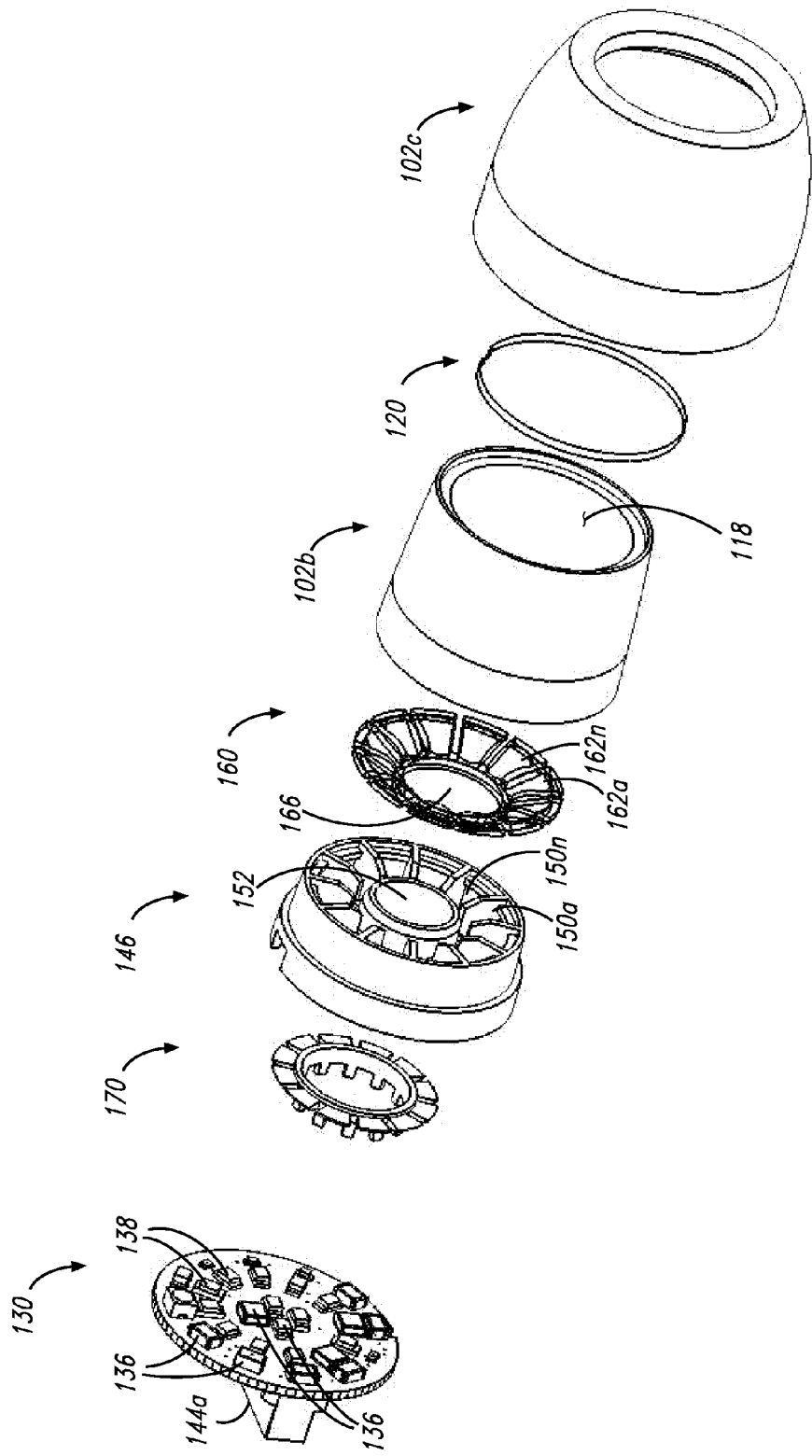
FIG. 3B is a partial exploded front, left side isometric view of the sampling device of FIGS. 1A-1D, according to another illustrated embodiment, showing the transducer PCB, light pipe, array of compartments, annular lens structure, tube, window and operational shroud.

FIGS. 3A and 3B show a portion of the sampling device 100 of FIGS. 1A-1D, illustrating various components in more detail.

In particular, FIGS. 3A and 3B show an interior of the passage 126 of the shroud 102c. The passage 126 is tapered to securely receive an outer perimeter of the lens tube 102b, for example, via a press fit, with the window or lens cover 120 secured therein.

FIGS. 3A and 3B also more clearly show details of the annular lens element 160, including the distinct lenses 162a, 162n (collectively 162), band 164 and inner diameter 166. The distinct lenses 162a are circumferentially arranged around the band 164 and extend radially outward from the band 164. Each of the distinct lenses 162a forms a tapered segment, the distal portion being generally wider than a portion proximate the band 164. The distinct lenses 162a also extend relatively forward of the band 164, a distance from the band 164 increasing as an imaginary path on the distinct lens 162 is traversed from a portion proximate the band 164 to a portion distal from the band 164. The distinct lenses 162a may further have a generally arcuate profile or cross-section taken along a major axis of the distinct lens 162, best illustrated in FIG. 3B. The annular lens element 160 in some ways resembles a flower, with the distinct lenses 162, 162n resembling petals. As previously noted, the segmentation of the distinct lenses 162 may be sized, dimensioned and oriented such that each distinct lens 162 is receivable by a respective one of the compartments 150 of the compartment structure 146.

FIGS. 3A and 3B also show the optional light-toned polymer insert 170, having segments sized, dimensioned and oriented to be received by respective compartments 150 of the compartment structure 146.

FIGS. 3A and 3B also show the transducer PCB 130, with coupler or connector 144a (FIG. 3A), temperature sensors 204 (FIG. 3A), emitters 134 (FIG. 3B), primary detectors or sensors 136 (FIG. 3B), and calibration detectors or sensors 138 (FIG. 3B).

Figure 4:
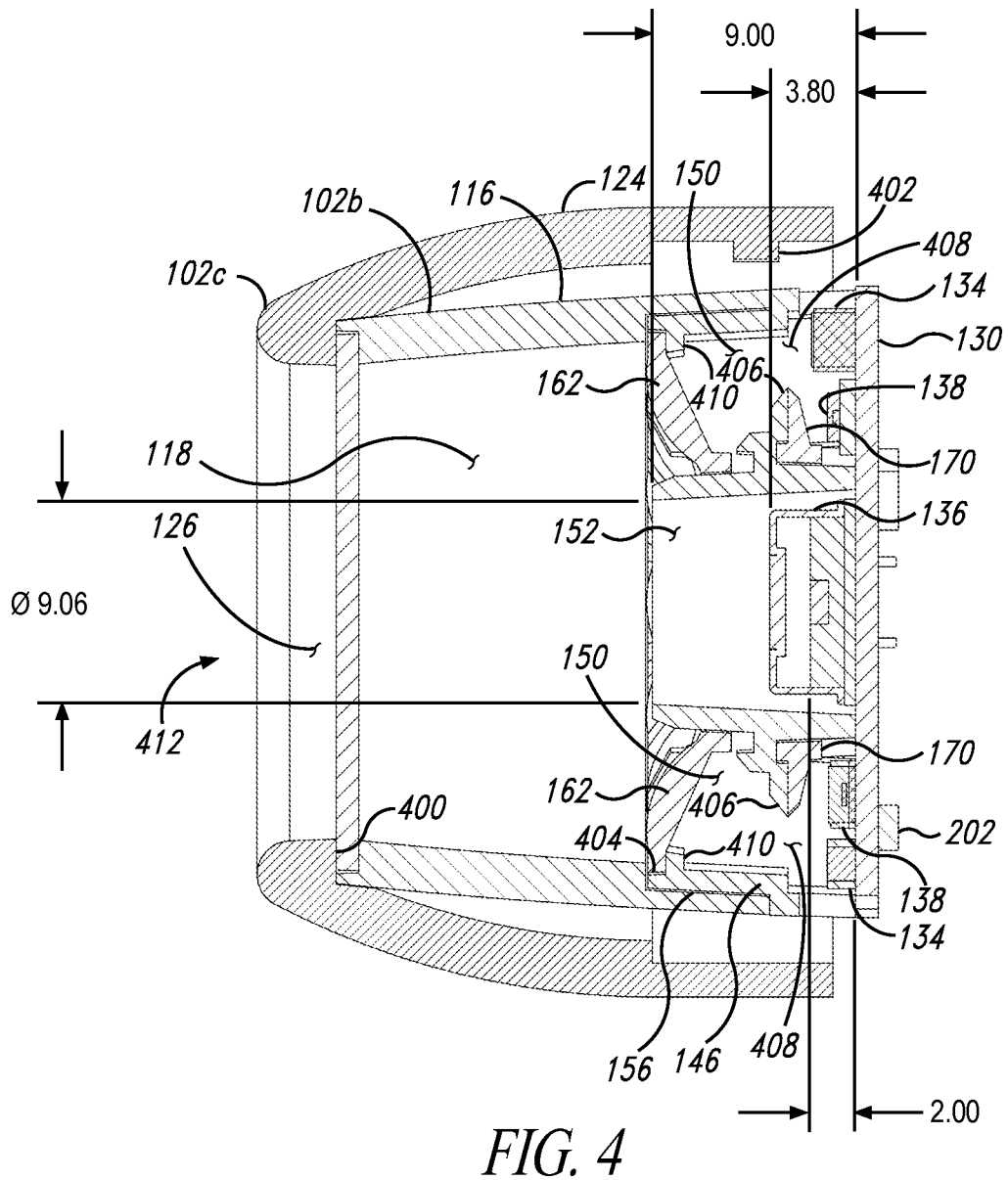
FIG. 4 is a cross sectional a portion of the sampling device of FIGS. 1A-1D, illustrating a relative positioning of the various components, according to one illustrated embodiment.

FIG. 4 shows a portion of the sampling device 100 of FIGS. 1A-1D, illustrating various components in more detail, and in particular the relative positioning of the various components.

As best illustrated in FIG. 4, a portion of an outer perimeter of the side wall 116 of the tubular lens 102b securely engages (e.g., press fit) a portion of an inner perimeter of a side wall 124 of the shroud 102c, proximate an internal flange 400. The securing engagement may be selectively releasable under a moderate application of pulling force or tension. The window or lens cover 120 is secured therebetween. The window or lens cover 120 may be flat, providing no magnification or focusing, but simply providing environmental protection to components rearward of the window or lens cover 120. In this embodiment, the shroud 102c may include one or more attachment structures 402 (e.g., slot or tab, only one shown).

The attachment structures 402 may allow selectively releasable attachment to another portion (e.g., platform visible in FIG. 1B) of the housing 102 (FIGS. 1A-1D). For example, attachment structures 402 may allow selectively releasable attachment to complementary attachment structures 154b (FIGS. 1A-1D, e.g., platform, slot or tab) on the main housing portion 102a.

As best illustrated in FIG. 4, an outer perimeter of an annular rim portion 156 of the compartment structure 146 securingly engages (e.g., press fit) a portion of an inner perimeter of a side wall 116 of the lens tube 102b, proximate an internal flange 404. The securing engagement may be selectively releasable under a moderate application of pulling force or tension.

As best illustrated in FIG. 4, the light-toned polymer insert 170 is positioned in the compartment structure 146, with a respective segment of the light-toned polymer insert 170 in a respective one of each of the compartments 150. In particular, the segments are positioned to cause some of the electromagnetic energy emitted by the respective emitters 136 to be directed (e.g., scattered, reflected) to the respective calibration detectors or sensors 138 in the respective compartment 150. As previously noted, other structures may be employed to direct electromagnetic energy toward the respective calibration detectors or sensors 138 in each compartment 150.

As best illustrated in FIG. 4, for each compartment 150 the compartment structure 146 includes a masking flange 406. The masking flange 406 masks the respective calibration detector or sensor 138 in the respective compartment. As illustrated in FIG. 4, the calibration detector or sensor 138 may be positioned underlying the respective masking flange 406. The masking flange 406 forms a slot 408, through which electromagnetic energy emitted by the respective emitter 134 can exit the respective compartment 150. In particular, the masking flange 406 includes a number of knife edges that form the slot(s) 408, severely limiting the ingress of electromagnetic energy into the compartment 150 from an exterior thereof, for instance from the ambient environment or returned from the sample or specimen.

By commonly housing emitters 134 with respective calibration detectors or sensors 138 in respective compartments 150, the sampling device may automatically take or capture an electromagnetic energy calibration sample or measurement each time an emitter emits electromagnetic energy. Such is performed in real-time, without any separate calibration mode. Such may be performed individually for each emitter, one at a time, as the emitter is activated. The thermal sensors 204 (FIG. 2D) may be sampled each time an emitter is activated. Alternatively, the thermal sensors 204 may be sampled periodically or aperiodically. The electromagnetic energy calibration sample or measurements and thermal calibration sample or measurements may be used to calibrate a detected or measured response. The electromagnetic energy calibration sample or measurements and thermal calibration sample or measurements may additionally or alternatively be used to control operation, for instance, to control a drive signal supplied to the emitters, or control an amplification applied to a signal produced or provided by the primary detectors or sensors 136. As discussed below, the electromagnetic energy calibration sample or measurements and thermal calibration sample or measurements may be processed on the sampling device 100, or sent to a separate component (e.g., digital computer) for processing.

As best illustrated in FIG. 4, the compartment structure 146 may include at least one flange 410 which at least partially supports the annular lens element 160. The distinct lenses 162 are positioned in respective compartments 150, oriented to focus electromagnetic energy emitted by the respective emitters 134 outwardly from the compartment 150 and front of the sampling device 100 (FIGS. 1A-1D). In particular, the distinct lenses 162 are positioned and oriented to focus electromagnetic energy toward a common or shared focal locus 412. As best illustrated in FIG. 5B, the shared focal locus may be positioned slightly forward of the window or lens cover 120.

As also illustrated in FIG. 4, a field-of-view of the primary detector(s) or sensor(s) 136 is aligned with a central passage 152 of the compartment structure 146, a passage 118 of the lens tube 102b, and a passage 126 of the shroud 102c. Such provides a transmissive path for electromagnetic energy returned from a sample or specimen to reach the primary detector(s) or sensor(s) 136.

FIG. 5A shows a portion of the sampling device of FIGS. 1A-1D, illustrating an annular segmented array or arrangement of emitters 134 and calibration detector(s) or sensor(s) 138.

In particular, FIG. 5A shows twelve emitters 134a-134l (collectively 134) radially arrayed along or about a perimeter 200 of the transducer PCB 130. FIG. 5A also shows twelve calibration detectors or sensors 138a-138l (collectively 138) radially arrayed along or about a perimeter 200 of the transducer PCB 130, spaced radially inwardly of the emitters. Each of the calibration detectors or sensors 138 is generally aligned with a respective one of the emitters along an imaginary line (broken line 500, only one called out in FIG. 5A) extending between the respective emitter 134 and a center of the array. As illustrated in FIG. 5A, walls 502 (only one called out in FIG. 5A) of the compartments 150 of the compartment structure 146 (FIGS. 1A-1D) delineate twelve radial segments.

As also illustrated in FIG. 5A, one or more primary detector(s) or sensor(s) 136 are positioned in a central region of the annular array. The central region can correspond to, or be aligned with, the central passage 152 of the compartment structure 146 (FIGS. 1A-1D), delineated by an inner perimeter wall 504 thereof.

While FIG. 5A shows twelve emitters 134, twelve calibration detectors or sensors 138, and twelve compartments 150 or annular radial segments, other embodiments may include fewer or greater number of emitters 134, calibration detectors or sensors 138 and/or compartments 150 or annular radial segments. As discussed above, some implementations may employ more than one emitter 134 in each set, compartment 150 or annular radial segment. Also as discussed above, some implementations may employ more than one calibration detectors or sensors 138 in each set, compartment 150 or annular radial segment. Thus, the total number of emitters 134, calibration detectors or sensors 138, and/or compartments 150 or annular segments should not be considered limiting. While FIG. 5A shows four primary detector(s) or sensor(s) 136, other embodiments may include fewer or greater number of primary detector(s) or sensor(s) 136.

FIG. 5B shows a schematic illustration of a portion of the sampling device of FIGS. 1A-1D in use, sampling a sample or specimen 506, according to one illustrated embodiment.

As illustrated in FIG. 5B, an emitter 134 emits electromagnetic energy in a compartment 150. The electromagnetic energy passes through a slot formed by a masking flange 170. As the ray drawing indicates, a distinct lens element 162 focuses the electromagnetic energy toward a focal locus 412. The focal locus is a point or set of points at which the various distinct lens elements 162 focus the emitted electromagnetic energy. Typically, the focal locus will be outward from the window or lens cover 120. In some implementations, the focal locus 412 will be forward or outward of the shroud 102c (FIGS. 1A-1D). In other implementations, the focal locus 412 will be rearward or within the passage 126 of the shroud 102c (FIGS. 1A-1D).

Representative exemplary dimensions of the embodiment shown in FIG. 5B, are as follows. A perpendicular distance from a position of a die of the emitter 134 to the lens element 162 is approximately 19 mm. A perpendicular distance from a top surface of the transducer PCB to the sample or specimen 506 is approximately 20 mm. A distance from a position of a die of the emitter 134 to the lens element 162 along an optical axis is approximately 7 mm. A distance from the lens element 162 to the sample or specimen 506 along the optical axis is approximately 15 mm. An included angle between the optical axis and a perpendicular line of symmetry (broke line) is approximately 32 degrees. A width of the lens element 162 is approximately 5 mm. A lateral distance between the die of the emitter 134 and the line of symmetry is approximately 12 mm. A total lateral distance from edge to edge (e.g., diameter of transducer PCB 130 is approximately 28 mm. A diameter of the bottom (e.g., portion closest to transducer PCB 130) of the passage 152 of the compartment structure 146 is approximately 10 mm.

As the ray drawing indicates, electromagnetic energy strikes the sample or specimen 506, and is scattered and/or reflected therefrom. A portion of the electromagnetic energy returns from the sample or specimen 506 to the sampling device 100 (FIGS. 1A-1D) and falls incident on, and thus is detected by, the primary detector(s) or sensor(s) 136. A portion of the electromagnetic energy returned from the sample or specimen 506 does not fall incident on, and thus is not detected by, the primary detector(s) or sensor(s) 136. In particular, the geometry of the sampling device 100 (FIGS. 1A-1D) causes at least some of the electromagnetic energy that is scattered from the sample or specimen 506 to be directed to the primary detector(s) or sensor(s) 136 via the passages 126, 118, 152. The geometry of the sampling device 100 (FIGS. 1A-1D) also causes a substantial portion of electromagnetic energy that is reflected or specular from the sample or specimen 506 to, for the most part, be directed away from the primary detector(s) or sensor(s) 136.

Figure 5C:
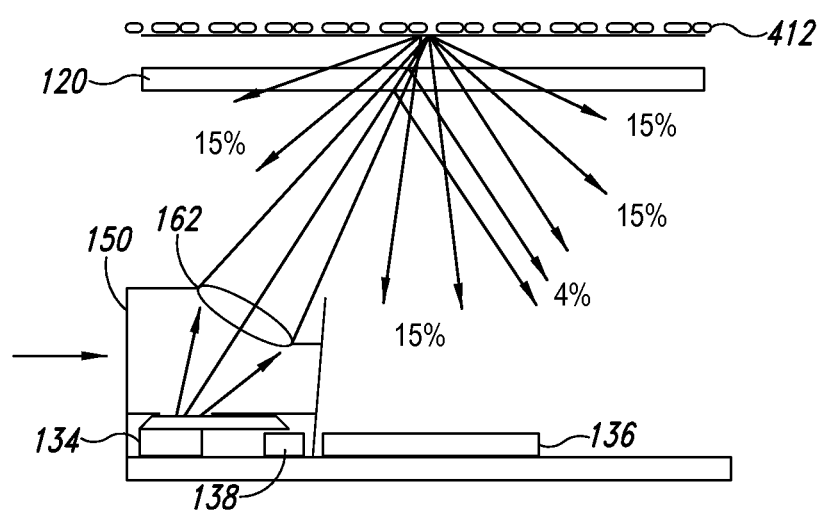
FIG. 5C is a schematic view of a portion of the sampling device of FIGS. 1A-1D illustrating exemplary emitted electromagnetic energy and returned of electromagnetic energy from a glossy red painted surface, according to one illustrated embodiment.

FIG. 5C shows a schematic illustration of a portion of the sampling device of FIGS. 1A-1D in use with a glossy red painted surface, according to one illustrated embodiment.

The glossy red painted surface may, as an example, have 15% Lambertian reflectance and 4% gloss or specular reflection.

As is readily apparent from the ray drawing, the geometry of the sampling device which arrays the emitters 134 in a generally annular array, locates the primary detectors or sensors 136 in a center of the annular array, and employs an annular lens structure 160 to focus the emitted electromagnetic energy to a common focal locus, substantially reduces or eliminates specular reflection from reaching the primary detectors or sensors 136. While much of the scattered electromagnetic energy is likewise lost, the scattered electromagnetic energy which does reach the primary detectors or sensors 136 is not longer mixed with the specular reflection. The specular reflection constitutes noise to the sampling device, the reduction of which can improve accuracy.

Thus, by suitably angling the projection of electromagnetic energy, specularly reflected light, both from a glossy target surface and from the protective window of the instrument, can be diverted away from the central zone where the primary detectors or sensors 136 are located.

While not required, the central passage 152 of the compartment structure 146 may taper from relatively wide to relatively narrow as the compartment structure 146 is traversed along its primary axis (e.g., longitudinal axis) from back to front, the most narrow portion the central passage 152 being at the first end 148a of the compartment structure 146, as illustrated in FIG. 5B.

While FIG. 5B includes certain dimension which may be suitable for some embodiments, the sampling device 100 may employ other dimensions. Thus, the specified dimensions should not be considered limiting.

Figure 6:
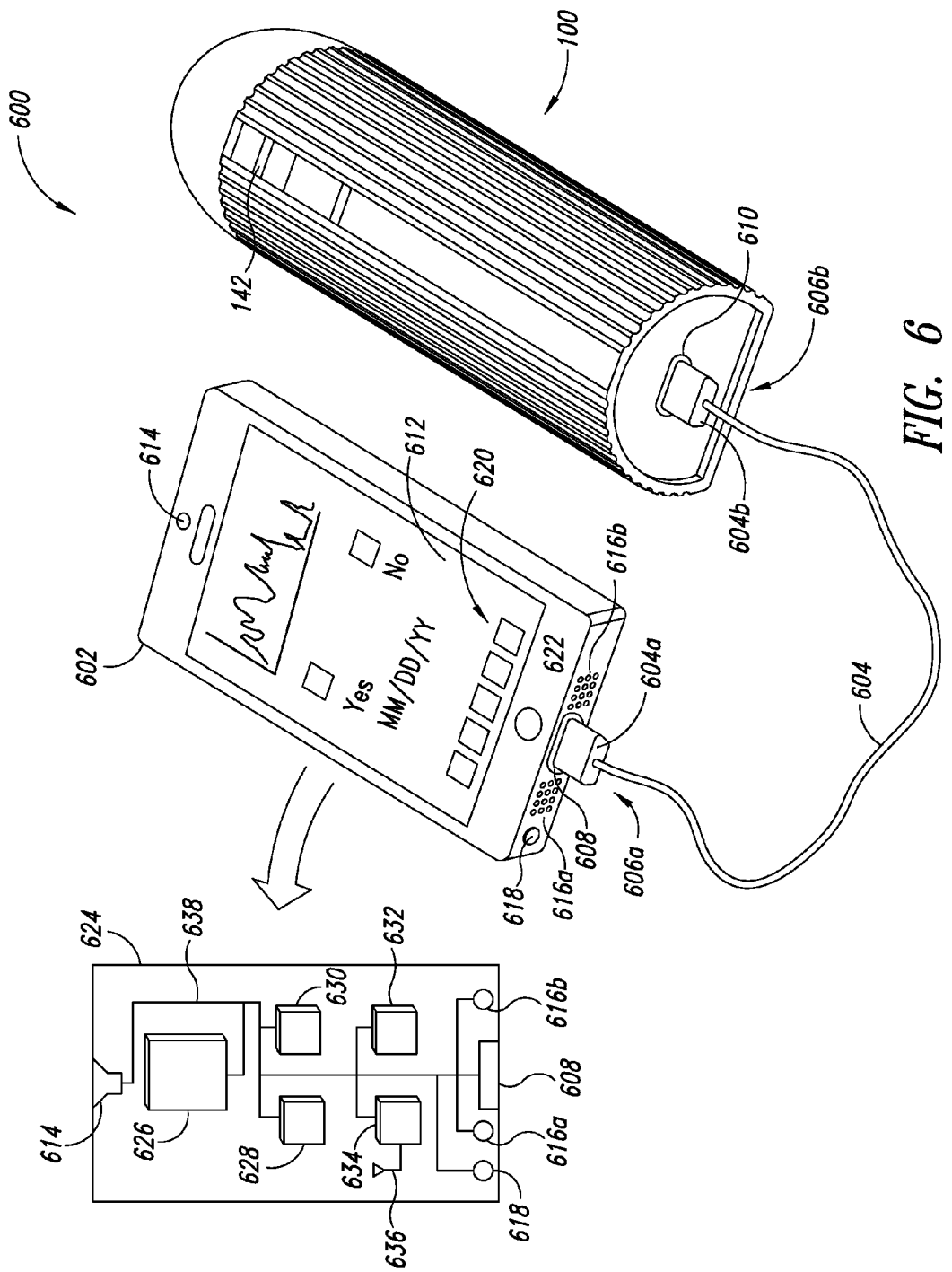
FIG. 6 is an isometric view of a sampling system that includes one or more sampling devices and one or more processor-based devices to which the sampling devices are communicatively coupled, according to one illustrated embodiment.

FIG. 6 shows a sampling system 600, according to one illustrated embodiment.

The sampling system 600 includes one or more sampling devices 100 (one shown). The sampling system 600 includes one or more processor-based device 602 (one shown). While illustrated as a mobile or handheld processor-based device 602, for instance, a Smartphone type device, the processor-based device 602 may take a large variety of other forms. For example, the mobile or handheld processor-based device 602 may take the form of the various computers or computing systems, such as a desktop or laptop personal computer, tablet computer, netbook computer, mini-computer, mainframe computer, or server computer.

The sampling device 100 is communicatively coupled to the processor-based device 602.

The sampling device 100 may be communicatively coupled to the processor-based device 602 via a physical communicative path such as a cable 604.

The cable 604 will typically include a connector proximate at least one end thereof, and often at both ends. For example, the cable 604 may have a first connector 604a (e.g., plug) at a first end 606a, the first connector 604a selectively detachably coupleable to a complimentary connector or port 608 on the processor-based device 602. Also, for example, the cable 604 may have a second connector 604b (e.g., plug) at a second end 606b, the second connector 604b selectively detachably coupleable to a complimentary connector or port 610 on the sampling device 100. Alternatively, the second end of the cable 604 may be permanently fixed to the sampling device 100. The physical ports and/or connectors 604a, 604b, 608, 610 and/or cables 604 may comply with any variety of physical and/or logical standards, and may incorporate one or more integrated circuits. For instance, the ports and/or connectors 604a, 604b, 608, 610 and/or cables 604 may comply with standards required of USB® standards or Apple Computer's Lighting® standards.

The cable 604 may, for instance, include a number of distinct electrical conductors (e.g., wires) (not shown) to provide signals between the sampling device 100 from the processor-based device 602. The electrical conductors may provide for bi-directional communications between the sampling device 100 and the processor-based device 602. The cable 604 may additionally provide electrical power (e.g., 5V, 10V) to the sampling device 100 from the processor-based device 602. In such an implementation, the sampling device 100 may omit any on-board consumable power source (e.g., primary or secondary chemical battery, ultra-capacitor, fuel cell) (not shown). Alternatively, the sampling device 100 may include a recharging circuit (not shown) that uses electrical power supplied via the cable 604 to recharge an onboard power source (e.g., secondary chemical battery, ultra-capacitor, fuel cell) (not shown).

The cable 604 may include one or more optical paths (e.g., optical fibers) (not shown). The optical paths may provide for bi-directional communications between the sampling device 100 and the processor-based device 602.

The sampling device 100 may be communicatively coupled to the processor-based device 602 via a wireless (e.g., radio frequency, microwave, visible or IR light) communicative path. As discussed below, many processor-based devices 602 include various radios or receivers, including ones that are compliant with cellular (e.g., CDMA, GSM, LTE), BLUETOOTH or WI-FI protocols. In such implementations, the sampling device 100 may include one or more radios or transceivers (not shown) that can be implemented as one or more integrated circuits and/or antennas (not shown). The integrated circuits and/or antennas (not shown) may be carried by the controller PCB 132 (FIGS. 1A-1D) or some other PCB, for instance, a dedicated communications PCB (not shown). In such implementations, the sampling device 100 will typically require an on-board consumable power source (e.g., primary or secondary chemical battery, ultra-capacitor, fuel cell) (not shown).

The sampling device 100 may be communicatively coupled via one or more networks (not shown) to various processor-based devices 600 and/or other sampling devices 100. The network may take a variety of forms including LANs, WANs, WLANs, WWANs, PSTN, to name a few. Such may, for example, allow access to one or more storage or databases of information. Such may, for example, allow updating or reconfiguration, for instance, by downloading of processor-executable instructions. Such may, for example, allow troubleshooting of the sampling device 100 should an error condition occur.

The processor-based device 602 may include a user interface which may, for example, include a touch-sensitive display 612, speakers 614 (one shown), microphone 616a, 616b (collectively 616), and/or audio output port 618. The user interface may also include user selectable icons, collectively 620, and/or one or more physical switches, keys or buttons 622.

FIG. 6 illustrates a PCB 624 of the processor-based device 602, removed therefrom to better illustrate various components housed within a housing of the processor-based device 602. The processor-based device 602 includes one or more processors, for instance, a microprocessor 626. The processor-based device 602 includes one or more nontransitory computer- or processor-readable media, for instance, ROM or Flash 628 and/or RAM 630.

The processor 626 employs instructions and or data from the ROM/Flash 628 and/or RAM 630 in controlling operation of the sampling device 100. For example, the processor 626 operates the emitters 134 (FIGS. 1A-1D) in one or more sequences. The sequences determine an order in which the emitters 134 (FIGS. 1A-1D) are turned ON and OFF. The sequences may also indicate an ordered pattern of drive levels (e.g., current levels, voltage levels, duty cycles) for the emitters 134 (FIGS. 1A-1D). Thus, for example, the processor 626 may cause the application of different drive levels to respective ones of the emitters 134 (FIGS. 1A-1D) to cause the emitters 134 (FIGS. 1A-1D) to emit in distinct bands of the electromagnetic spectrum. The processor 626 may process information generated by the primary detector(s) or sensor(s) 136 (FIGS. 1A-1D), which is indicative of the response by at least a portion of a sample or specimen to illumination by the emitters 134 (FIGS. 1A-1D). The information at any given time may be indicative of the response by the sample or specimen to illumination by one or more of the emitters 134 (FIGS. 1A-1D). Thus, the information over a period of time may be indicative of the responses by the sample or specimen to sequential illumination by each of a plurality of the emitters 134 (FIGS. 1A-1D), where each of the emission spectra of each of the emitters 134 (FIGS. 1A-1D) has a different center, bandwidth and/or other more complex differences in spectral content, such as those described above (e.g., width of the band, the skew of the distribution, the kurtosis, etc.).

The processor 626 employs instructions and or data from the ROM/Flash 628 and RAM 630 to perform analysis or evaluation of the responses. For example, the processor 626 may compare a response to one or more reference responses. The processor 626 may determine whether a response from a sample or specimen sufficiently matches the signature responses from a reference sample or specimen. Such may, for example, be employed to detect a presence or absence of a substance, for instance, an illegal substance (e.g., cocaine), an explosive substance (e.g., nitrate based), or a toxic substance (e.g., carcinogens). The processor 626 may cause display of a result of an analysis or evaluation. For instance, the processor 626 may cause display of a simple indicator (e.g., check, YES/NO, other text, GREEN/RED/AMBER or other color) indicative of the result. Also, for instance, the processor 626 may cause display of a more complex indicator (e.g., graph, table chart) indicative of the result. Additionally or alternatively, the processor 626 may cause an aural indication indicative of a result via speaker 614, for example a sound such as a beep, buzz, or even spoken or synthesized words.

The processor-based device 602 may additionally include a display driver 632, communicatively coupled to drive the touch-sensitive display 612 and/or detect touches, swipes or other user inputs via the touch-sensitive display 612. The display driver 632 may be a dedicated integrated circuit, for example, a graphical processing unit.

The processor-based device 602 may additionally include one or more radios or transceivers 634 (only one shown) and one or more associated antennas 636 (only one shown). The radios or transceivers 634 and antennas 636 may take any of a large variety of forms, for example, ones suitable for wireless communications such as cellular communications (e.g., CDMA, GSM, LTE), BLUETOOTH communications and/or WI-FI communications.

The processor-based device 602 may additionally include one or more accelerometers or gyroscopes. Such components may be capable of producing data indicative of an orientation of the processor-based device 602. Such components may be capable of producing data indicative of a speed, movement or acceleration of the processor-based device 602.

The various components may be communicatively coupled via one or more buses 638 (only one shown) or other connections, for example, data buses, instruction buses, address buses, power buses, etc.

FIGS. 7A and 7B show a calibration cap 700, for optional use with a sampling device 100, according to one illustrated embodiment.

The calibration cap 700 is selectively removably coupleable to a front of the sampling device 100. For example, the calibration cap 700 may be selectively removably coupleable to the shroud 102c (FIGS. 1A-1D). Alternatively, the calibration cap 700 may be selectively removably coupleable to the lens tube 102b (FIGS. 1A-1D), in place of the shroud 102c (FIGS. 1A-1D), the shroud 102c removed to allow physical coupling of the calibration cap 700. The calibration cap 700 may be coupled via a press fit, or alternatively a detent or some other coupler structure (e.g., bayonet mount, screw or threaded mount).

The calibration cap 700 includes a side wall 702 which delimits a central passage 704, the central passage 704 open at a distal proximal end 706 of the calibration cap 700 to the passage 118 of the lens tube 102b. The side wall 702 may comprise a plastic, which may enhance the ability to use a press fit.

The calibration cap 700 includes a calibration or reference target, sample or specimen 708 positioned at a distal end 710 of the calibration cap 700. The calibration or reference target 708 has known and stable optical characteristics. Thus, the sampling device 100 may take calibration samples using the known calibration or reference target 708. Such may allow detection of drift in operation of various components. For example, such may allow detection of drift in operation of the emitters 134. Such may also allow detection of drift in operation of the primary detectors or sensors 136. Even more importantly, such may allow detection of drift in operation of the calibration detectors or sensors 138, which would not otherwise be possible.

As previously explained, the calibration detectors or sensors 138 may be used to automatically calibrate for drift in operation of the emitters 134 and primary detectors or sensors 136, for instance each time an emitter emits electromagnetic energy. In contrast, the calibration cap 700 may be used from time-to-time (e.g., periodically, aperiodically) to calibrate for drift in operation of the emitters 134, primary detectors or sensors 136, and/or calibration detectors or sensors 138. For example, the calibration cap 700 may at the start of each day, at the start of each hour, weekly, monthly, or before sampling of each sample or specimen.

The sampling device 100 may provide an alert if a condition is detected, for which condition the sampling device 100 is not capable of automatically adjusting to compensate or accommodate, for instance a condition outside a range of adjustable conditions. The sampling device 100 may provide an alert even if a detected condition is one for which the sampling device 100 automatically adjusts to accommodate or compensate. The sampling device 100 may calibration data or information remotely, for example, to one or more processor-based devices 602 (FIG. 6) such as a Smartphone device (e.g., iPhone®, Andriod® based Smartphone).

CONCLUDING REMARKS

As used herein and in the claims, longitudinal refers to the major dimension or length of a structure, and is not limited to being an axis of revolution of a profile or cross-section of such structure.

As used herein and in the claims, the term "non-transitory computer-readable medium" and "non-transitory processor-readable medium" are used interchangeably to refer to any tangible medium that participates in providing instructions for execution or storage of data, parameters or other information. Such a medium may take many forms, including but not limited to, non-volatile media and volatile media. Non-volatile media includes, for example, hard, optical or magnetic disks 161, 166, 168, respectively. Volatile media includes dynamic memory, such as system memory 150. Common forms of computer- or processor-readable media include, for example, floppy disk, flexible disk, hard disk, magnetic tape, or any other magnetic medium, CD-ROM, any other optical medium, punch cards, paper tape, any other physical medium with patterns of holes, RAM, PROM, EPROM, EEPROM, FLASH memory, any other memory chip or cartridge, or any other tangible medium from which a computer or processor can read.

While not illustrated, the sampling device 100 (FIGS. 1A-1D) may include one or more elements operable to deflect or otherwise position the emitted or received electromagnetic energy. The elements may, for example, include one or more optical elements, for example, lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, for example permanent magnets or electromagnets such as those associated with cathode ray tubes and/or mass spectrometers.

While generally illustrated and described in a standalone form factor, which may, or may not, be communicatively coupled to a processor-based device (e.g., smartphone, tablet computer, netbook computer, laptop computer, desktop computer), the sampling device 100 (FIGS. 1A-1D) may have other form factors. For example, the sampling device 100 (FIGS. 1A-1D) may be integrated into a smartphone, the various PCBs and other components located in a smartphone housing or shell to form an integral device. Likewise, the sampling device 100 (FIGS. 1A-1D) may be integrated into other processor-based devices. Such may allow omission of one or more components from the PCBs, which may rely on components of the processor-based device to avoid duplication, and thereby reducing costs, size and/or complexity.

While generally illustrated and described as having a single emitter 134 per compartment 150, in some implementations there may be more than one emitter in any given compartment 150. For instance, there may be two emitters 134 with adjacent or even overlapping ranges of wavelengths, for instance to cover the N-IR portion of the electromagnetic spectrum. Thus, any given calibration detector or sensor 138 may receive electromagnetic energy from two or even more emitters 134, where the calibration detector or sensor 138 has a sensitivity or responsive range that covers the range of wavelengths of the emitters 134. Such may advantageously reduce parts count, complexity, size, and importantly cost. Suitable calibration detector or sensor 138 may in some instances cost over $60, so the ability to omit one or more calibration detector or sensor 138 is highly advantageous.

While generally illustrated and described as employing separate transducer PCB 130 and controller PCB 132, the sampling device 100 (FIGS. 1A-1D) may employ a single PCB, or may employ more than two PCBs. Further, various components illustrated on one PCB, may be carried by the other PCB, or in some instances omitted. Alternatively or additionally, the various components on one PCB 130, 132 or both PCBs 130, 132 can be implemented in a system on chip (SoC) integrated circuit structure, reducing the parts count as well as the number of PCBs.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to: U.S. Pat. Nos. 7,996,173; 8,081,304; and 8,076,630; U.S. Provisional Patent Application Ser. Nos. 60/623,881, filed Nov. 1, 2004; 60/732,163, filed Oct. 31, 2005; 60/820,938, filed Jul. 31, 2006; 60/834,662, filed Jul. 31, 2006; 60/834,589, filed Jul. 31, 2006; 60/871,639, filed Dec. 22, 2006; 60/883,312, filed Jan. 3, 2007; 60/890,446, filed Feb. 16, 2007; 61/538,617, filed Sep. 23, 2011; 61/597,586, filed Feb. 10, 2012; 61/597,593, filed Feb. 10, 2012; 61/760,527, filed Feb. 4, 2013; and 61/767,716, filed Feb. 21, 2013, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sampling system, comprising:
a sampling device, the sampling device including:
a housing;
a plurality of emitters received in the housing, each of the emitters selectively operable to emit electromagnetic energy in a respective range of wavelengths in an optical portion of the electromagnetic spectrum, the ranges of wavelengths of at least some of the emitters different from the ranges of wavelengths of others of the emitters;
an endless array of compartments which isolate each of a number of the emitters from one another;
at least one primary sampling sensor received in the housing and positioned to receive electromagnetic energy returned to the sampling device by a sample, if any, illuminated by the electromagnetic energy emitted by at least one of the emitters, the at least one primary sampling sensor responsive to a number of wavelengths of electromagnetic energy returned to the sampling device; and
a plurality of calibration sensors received in the housing, each of the calibration sensors positioned in a respective one of the compartments of the endless array of compartments to receive electromagnetic energy emitted by at least one of the emitters substantially free of electromagnetic energy returned to the sampling device, the at least one calibration sensor responsive to a number of wavelengths of electromagnetic energy emitted by the emitters.

2. The sampling system of claim 1 wherein the plurality of calibration sensors comprises at least one calibration sensor per emitter.

3. The sampling system of claim 2 wherein the calibration sensors are matched to the output of the respective emitters.

4. The sampling system of claim 1 wherein the endless array of compartments are formed as a unitary single-piece annular array arranged about a central passage.

5. The sampling system of claim 1 wherein each compartment includes a slot that limits entrance into the respective compartment of spectral illumination returned to the sampling device from the sample, if any.

6. The sampling system of claim 5 wherein the respective calibration sensors are positioned in the respective compartments shielded from the respective slots.

7. The sampling system of claim 1 wherein the compartments each have walls, the entirety of the walls colored black.

8. The sampling system of claim 7, further comprising:
at least one optical tap that provides a respective distinct optical path between a position at least proximate respective ones of the emitters and respective ones of the calibration sensors.

9. The sampling system of claim 8 wherein the at least one optical tap is an integral portion of the endless array of compartments.

10. The sampling system of claim 8 wherein the at least one optical tap comprises cyclic polyolefin.

11. The sampling system of claim 1 wherein the compartments each have walls, a portion of the walls colored black and a portion of the walls colored a reference color.

12. The sampling system of claim 1 wherein the calibration sensors are matched to the output of the respective emitter with which the calibration sensor is compartmentalized.

13. The sampling system of claim wherein the calibration sensors each consist of a single optical sensor chip that detects from near-infrared (N-IR) through near-ultraviolet (N-UV) wavelengths of electromagnetic energy.

14. The sampling system of claim 1, further comprising:
a first circuit board on which the emitters are arrayed in a circular array; and
an annular array of distinct lenses physically coupled to one another as an integral one-piece construction which includes a circular band that physically couples the distinct lenses to one another, each of the distinct lenses closely received in a respective one of the compartments of the endless array of compartments.

15. The sampling system of claim 14 wherein the at least one primary sampling sensor is carried by the first circuit board disposed centrally with respect to the circular array of the emitters.

16. The sampling system of claim 1, further comprising:
at least one temperature sensor positioned to sense a temperature at least proximate the at least one of the emitters or the at least one primary sampling sensor, and responsive thereto to produce signals indicative of a sensed temperature.

17. The sampling system of claim 1, further comprising:
at least one control subsystem housed separately from the sampling device, and communicatively coupled to receive sensor information at least from the at least one primary sampling sensor and the at least one calibration sensor.

18. The sampling system of claim 17 wherein the at least one control subsystem is communicatively coupled to control the emitters.

19. The sampling system of claim 18 wherein the sampling device further includes:
at least one temperature sensor positioned to sense a temperature at least proximate the at least one of the emitters or the at least one primary sampling sensor, and responsive thereto to provide signals indicative of a sensed temperature to the at least one control subsystem that is housed separately from the sampling device.

20. The sampling system of claim 19 wherein the at least one control subsystem calibrates an output value based at least in part on information from both the calibration sensors and the at least one temperature sensor.

21. The sampling system of claim 19 wherein the at least one control subsystem calibrates a drive signal supplied to at least one of the emitters based at least in part on information from both the calibration sensors and the at least one temperature sensor.

22. The sampling system of claim 17 wherein the at least one control subsystem is a smartphone.

23. The sampling system of claim 1 wherein the sampling device further includes:
at least one control subsystem received in the housing, the at least one control subsystem communicatively coupled to control the emitters, and communicatively coupled to receive sensor information at least from the at least one primary sampling sensor and the at least one calibration sensor.

24. The sampling system of claim 23 wherein the sampling device further includes:
at least one temperature sensor communicatively coupled to the at least one control subsystem, the at least one control subsystem controls operation based at least in part on information from both the calibration sensors and the at least one temperature sensor.

25. The sampling system of claim 24 wherein the at least one temperature sensor comprises a plurality of temperature sensors, at least one of the temperature sensors positioned to sense a temperature at least proximate the at least one of the emitters or the at least one primary sampling sensor.

26. The sampling system of claim 24 wherein the at least one control subsystem calibrates an output value based at least in part on information from both the calibration sensors and the at least one temperature sensor.

27. The sampling system of claim 24 wherein the at least one control subsystem calibrates a drive signal supplied to at least one of the emitters based at least in part on information from both the calibration sensors and the at least one temperature sensor.

28. The sampling system of claim 1, further comprising:
at least one window that is transmissive to at least some of the wavelengths of electromagnetic energy emitted by the emitters and that provides passage of the wavelengths of electromagnetic energy emitted by the emitters out of an interior of the housing to an exterior of the housing and passage of the wavelengths of electromagnetic energy returned to the sampling device from the exterior of the interior of the housing.

29. The sampling system of claim 1, further comprising:
a single user manipulable switch, operation of which causes the sampling device to sample a specimen.

30. The sampling system of claim 29 wherein the sampling device automatically provides a signal indicative of information sensed by the primary sampling sensors and the calibration sensors to a remotely housed control subsystem in response to user activation of the user manipulable switch.

31. The sampling system of claim 1 wherein the respective range of wavelengths of at least two of the emitters at least partially overlap.

32. A sampling device operable to sample specimens, the sampling device comprising:
a housing having a first end, a second end, and a sampling aperture at least proximate the first end;
a plurality of emitters at least partially housed by the housing and arrayed about a first location, the emitters selectively operable to emit electromagnetic energy in respective ranges of wavelengths, the ranges of wavelengths of at least some of the emitters different from the ranges of wavelengths of others of the emitters;
a first circuit board on which the emitters are arrayed in a circular array;
an endless array of compartments which isolate each of the emitters from one another;
a plurality of calibration sensors, each of the calibration sensors positioned in a respective one of the compartments of the endless array of compartments;
at least one annular lens structure at least partially housed by the housing, the at least one annular lens structure positioned with respect to the emitters and the sampling aperture to focus electromagnetic energy emitted by the emitters outwardly from the sampling aperture toward a focal locus; and
at least one primary sampling sensor at least partially housed by the housing at least proximate the first location and positioned to receive electromagnetic energy returned to the sampling device from a specimen, if any, positioned at the focal locus via the sampling aperture, the at least one primary sampling sensor responsive to at least some of the electromagnetic energy returned to the sampling device via the sampling aperture.

33. The sampling device of claim 32 wherein the emitters are arrayed in a circular array and the at least one annular lens structure includes an annular array of distinct lenses physically coupled to one another.

34. The sampling device of claim 33 wherein the annular array of distinct lenses takes the form of an integral one-piece construction which includes a circular band that physically couples the distinct lenses to one another.

35. The sampling device of claim 34 wherein the distinct lenses each extends radially outwardly from the circular band at an angle with respect to a plane defined by the circular band.

36. The sampling device of claim 33 wherein the annular array of lenses comprises a material that does not distort electromagnetic energy in a near-ultraviolet (N-UV) portion of the electromagnetic spectrum.

37. The sampling device of claim 32 wherein the at least one annular lens structure comprises cyclic polyolefin.

38. The sampling device of claim 32 wherein the at least one annular lens structure comprises a silica material.

39. The sampling device of claim 32 wherein the endless array of compartments are formed as a unitary single-piece construction and are arranged about a central passage.

40. The sampling device of claim 39 wherein the at least one annular lens structure includes an annular array of distinct lenses physically coupled to one another as an integral one-piece construction which includes a circular band that physically couples the distinct lenses to one another, each of the distinct lenses closely received in a respective one of the compartments of the endless array of compartments.

41. The sampling device of claim 32 wherein the housing includes a body portion and a lens tube portion that extends from the body portion, the body portion having an interior with an opening, the first circuit board mounted across the opening of the body portion.

42. The sampling device of claim 41, further comprising:
a second circuit board received in a cavity of the housing, the second circuit board carrying control circuitry communicable coupled to the emitters and at least one primary sampling sensor.

43. The sampling device of claim 41, further comprising:
a window across the sampling aperture, the window transmissive to at least some wavelengths of electromagnetic energy.

44. The sampling device of claim 43 wherein the housing includes a shroud that extends from the lens tube outwardly of the sampling aperture and the window, and which shrouds the sampling aperture and the window.

45. The sampling device of claim 32 wherein each compartment has a slot to limit entrance into the respective compartment of spectral illumination returned to the sampling device from the specimen, if any, and each of the respective calibration sensors is positioned to be shielded from the respective slot.

46. The sampling device of claim 32, further comprising:
at least one optical calibration tap that provides a respective distinct optical path between a position at least proximate respective ones of the emitters and respective ones of the calibration sensors.

47. The sampling device of claim 46 wherein the at least one optical calibration tap is an integral portion of the endless array of compartments.

48. The sampling device of claim 47 wherein the at least one optical calibration tap is a light-toned polymer insert.

49. The sampling device of claim 32 wherein the calibration sensors are matched to the output of the respective emitter with which calibration sensor is compartmentalized.

50. The sampling device of claim 49 wherein the calibration sensors each consist of a single optical sensor chip that detects from near-infrared (N-IR) through near-ultraviolet (N-UV) wavelengths of electromagnetic energy.

51. The sampling device of claim 32 wherein the at least one annular lens structure focuses the electromagnetic energy emitted by the emitters such that the at least one primary sampling sensor receives electromagnetic energy returned to the sampling device from the specimen via Rayleigh scattering, substantially free of electromagnetic energy returned to the sampling device from the specimen via Raman scattering.

52. The sampling device of claim 32 wherein the at least one primary sampling sensor consists of a single optical sensor chip that detects from near-infrared (N-IR) through near-ultraviolet (N-UV) wavelengths of electromagnetic energy.

53. The sampling device of claim 32 wherein the respective range of wavelengths of at least two of the emitters at least partially overlap.

54. The sampling device of claim 32, further comprising:
a calibration cap having a calibration target, the calibration cap removably physically coupleable to position the calibration target in a field of view of the optical emitters and the at least one primary sampling sensor.

* * * * *